United States Patent [19]
Racie et al.

[11] Patent Number: 6,165,748
[45] Date of Patent: Dec. 26, 2000

[54] FRAZZLED NUCLEOTIDE SEQUENCES AND EXPRESSION PRODUCTS

[75] Inventors: Lisa Racie, Acton; Edward Lavallie, Tewksbury; Janet Paulsen, Watertown; Hazel Sive, Newton; Benjamin Sun, Cambridge, all of Mass.

[73] Assignees: Genetics Institute, Inc.; Whitehead Institute for Biomedical Research, both of Cambridge, Mass.

[21] Appl. No.: 08/893,654

[22] Filed: Jul. 11, 1997

[51] Int. Cl.$^7$ ............................. C12N 15/10; C12N 15/12; C12N 5/10; C07K 14/71

[52] U.S. Cl. ..................... 435/69.1; 435/320.1; 435/325; 435/252.3; 435/254.11; 536/23.1; 536/23.5; 530/350; 530/300

[58] Field of Search .................................. 536/23.1, 23.5; 530/300, 350; 435/69.1, 320.1, 325, 252.3, 254.11

[56] References Cited

FOREIGN PATENT DOCUMENTS

WO 97/48275   12/1997   WIPO.

OTHER PUBLICATIONS

Bellaïche and Perrimon, *Medecine/Sciences* 13:166–74 (1997).
Finch et al., PNAS USA 94:6770–6775 (1997).
Miller et al., Genetic Engineering (Plenum Press), vol. 8, pp. 277–298 (1986).
Blankesteijn et al., Circulation 92(8):P. 2191 (Abstract) (1995).
Kologziej et al., Cell 87:197–204 (1996).
Wang, et al., Hum. Mol. Cenet. 6(3):465–472 (1997).
Leyns et al., Cell 88:747–756 (1997).
Blankesteijn et al., Nature Medicine 3(5):541–544 (1997).
Rattner et al., PNAS USA 94:2859–2863 (1997).
Wang et al., Cell 88:757–766 (1997).
Cadigan and Nusse, Biochimica et Biophysica Acta 1332:R1–R5 (1977).
Strutt et al. Nature 387:292–295 (1997).
Ito and Sokol, Mechanisms of Development 61:113–125 (1997).
Bhanot et al., Nature 382:225–230 (1996).
Blankesteijn et al., J. Mol. Cell Cardiol. 28:1187–1191 (1996).
Orsulic and Peifer, Current Biology 6(11):1363–1367 (1996).
Snyder et al., Curr. Biol. 6(10):1302–1306 (1996).
Wang et al., J. Biol. Chem. 271(8):4468–4476 (1996).
Li et al., Genes & Development 9:2821–2830 (1995).
Hoang et al., J. Biol. Chem. 271(42):26131–26137 (1996).
Ingham, Trends in Genetics 12(10):382–385 (1996).
He et al., Science 75:1652–1654 (1997).
Sawa et al., Genes Dev. 10:2189–2197 (1996).
Shirozu et al., Genomics 37:273–280 (1996).
Alcedo et al., Cell 86:221–232 (1996).
Zhao et al., Genomics 27:370–373 (1995).
Park et al., Mech. Dev. 45:127–137 (1994).
Adler et al., Mech. Dev. 46:101–107 (1994).
Park et al., Dev. Gen. 15383–389 (1994).
Krasnow and Adler, Development 120:1883–1893 (1994).
Gething and Sambrook, Nature 293:620–625 (1981).
Morinaga et al, Bio/Technology 84:636–639 (1984).
Taniguchi et al., PNAS USA 77(9):5230–5233 (1980).
Kaufman and Sharp, J. Mol. Biol. 159:601–621 (1982).
Kaufman et al., Mol. Cell. Biol. 5:1750–1759 (1985).
Gough et al., EMBO J. 4(3):645–653 (1985).
Okayama and Berg, Mol. Cell. Biol. 2(2):161–170 (1982).
Geli et al., PNAS USA 82:689–693 (1985).
Wong et al., Science 228:810–815 (1985).
Jacob and Pattabiraman, J. Biosci. 6(3):289–295 (1984).
Metsäranta et al., Dev. Dynamics 204:202–210 (1995).
Ayala et al., Modern Genetics, 2nd ed., Benjamin/Cummings: Menlo Park, CA, glossary, 1980.
Deutsch and Busson, 1997, médecine/sciences 13:222–224.
Prowse et al., Molecular characterization and acute phase expression of the multiple Mus caroli alpha 1–acid glycoprotein (AGP) gene, J. Biol. Chem., 265(18): 10201–10209, Jun. 1990.
Chan et al., Two homologs of the Drosophila polarity gene frizzled (fz) are widely expressed in mammalian tissue, J. Biol. Chem., 267(35): 25202–25207, Dec. 1992.
Finch et al., GenBank Accession Number AF001900, Jun. 28, 1997.
GenBank Accession Number L02529, accessed Apr. 1998, Jul. 16, 1993.

*Primary Examiner*—Lorraine Spector
*Assistant Examiner*—Claire M. Kaufman
*Attorney, Agent, or Firm*—Barbara A. Gyure

[57] ABSTRACT

Purified Frazzled proteins, including WG67-16, WG67-19 and WA628, and processes for producing them are disclosed. DNA molecules encoding the Frazzled proteins, including WG67-16, WG67-19 and WA628, are also disclosed. The proteins may be used in modulating the binding of Wnt genes to their receptor. They are useful in the modulation of cellular formation, growth, differentiation, proliferation and/or maintenance of a variety of adult and embryonic tissues and organs.

39 Claims, No Drawings

FRAZZLED NUCLEOTIDE SEQUENCES AND EXPRESSION PRODUCTS

The present invention relates to the Frazzled protein family, DNA encoding the members of this family, processes for obtaining them, and methods of using them. These proteins may be used to induce expression of factors in and/or differentiation of various tissues and organs, and particularly, inducing formation, growth, differentiation, proliferation and/or maintenance of various tissues and organs. The proteins are useful in the treatment of various disorders associated with defects in cellular formation, growth, differentiation, proliferation and/or maintenance of these various tissues and organs including, for example, brain, lung, pancreas, liver, spleen, kidney, intestines and/or other tissues and organs. The proteins are also useful in the modulation of cellular formation, growth, differentiation, proliferation and/or maintenance of tissues and organs. These proteins are also useful for augmenting the activity of other tissue and organ regenerating and differentiation factors. In particular the proteins are useful in modulating haemotopoiesis, and in modulating the development of gut, neuronal, brain and muscle tissues.

BACKGROUND OF THE INVENTION

The search for molecule(s) responsible for the formation, proliferation, differentiation and maintenance of tissues and organs, such as haematopoietic, gut, neuronal, brain and muscle tissues, has been extensive as there is a tremendous need for factors useful for treating conditions involving degradation or damage to these tissues, as well as various disorders associated with defects in these processes. The present invention relates to a family of proteins designated as Frazzled, which family shares homology to the ligand binding domain of the Frizzled proteins family.

The structures of several proteins encoded by a gene family designated as frizzled, have previously been elucidated. Frizzled protein family members have been shown to bind to the Wingless (Wg) protein, the Drosophila prototype of the Wnt family. Bhanot et al., Nature, 382:225–230 (1996). In mammals and other species, the Frizzled family of proteins are membrane bound receptor molecules which bind proteins produced by the family of wnt genes. Wang et al., J. Biol. Chem., 271:4468–4476 (1996). Wnt genes play multiple roles in cell proliferation and differentiation and are expressed in a variety of adult and embryonic tissues and organs, for example, brain, lung, pancreas, liver, spleen, kidney, intestines and/or other tissues and organs.

Several Frizzled-related genes (frzbs) have been identified which encode proteins resembling Frizzleds, i.e., receptors lacking most of the transmembrane domain(s). It has been postulated that Frzbs function as soluble antagonists of Wnt signals. Hoang, et al., JBC 271:26131 (1996), identified a frizzled homologue (which they named frzb) expressed primarily in the cartilaginous cores of developing long bones which was thought to be involved in morphogenesis of the mammalian skeleton. Unlike the genes encoding the Frizzled family of proteins, the frzb gene does not contain seven transmembrane domains. The bovine and human Frzb are 94% identical. Ratner, et al., PNAS 94:2859 (1997) identified in mouse eye cDNA libraries three DNA sequences encoding secreted frizzled-related proteins (sFRP-1, SFRP-2, and sFRP-3). Wang, et al., Cell 88:757 (1997), isolated a Xenopus homologue of Frzb containing an amino-terminal Frizzled motif and which was soluble and secretable. It was also found to bind and inhibit Wnt-8 (a ventral inducer) and to act as a functional inhibitor of Wnt signalling through direct extracellular binding. Leyns, et al., Cell 88:747 (1997), have identified a secreted protein, Frzb-1, also having sequence similarity to the extracellular domain of Frizzled.

SUMMARY OF THE INVENTION

The present invention provides novel DNA sequences encoding novel members of a novel protein family termed Frazzled. In particular embodiments, the present invention provides novel DNA sequences encoding Frazzled proteins including, but not limited to WG67-16, WG67-19 and WA628. The nucleotide sequences, and the corresponding amino acid sequences encoded by these DNA sequences, are provided in the Sequence Listings. In particular, the present invention comprises isolated DNA sequences, encoding a Frazzled protein comprising a DNA sequence selected from the group consisting of: nucleotides #44 through #889 of SEQ ID NO: 1; nucleotides #8 through #850 of SEQ ID NO: 3; and nucleotides #80 through #967 of SEQ ID NO: 5; as well as nucleotide sequences comprising sequences that encode the amino acid sequences of SEQ ID NO 13–18; as well as fragments and variants of the above nucleotide and amino acid sequences which are readily obtainable from the above and which retain Frazzled activity. The present invention further comprises sequences which hybridize to these sequences under stringent hybridization conditions and encode a protein which exhibits Frazzled activity. In a presently preferred embodiment, these sequences hybridize to SEQ ID NO 15, 16 17, and/or 18 under stringent hybridization conditions that include, for example, the use of initial low stringency hybridization conditions (such as 6X SSC, 0.5% SDS, at about 60° C.), overnight which is followed by a higher stringency wash condition (such as 2XSSC, 0.1% SDS, at about 20° C.) or an even higher stringency wash (such as 0.1XSSC, 0.1% SDS, at about 65° C., for less than an hour).

The present invention also provides methods for formation, proliferation, differentiation, and maintenance of a variety of adult and embryonic tissues and organs including, for example, haematopoietic, gut, neuronal, muscle, brain, lung, pancreas, liver, spleen, kidney, intestines and/or other tissues and organs. Also the proteins of the invention may be used to induce expression of factors in and/or differentiation of a variety of adult and embryonic tissues and organs, and particularly, to induce formation, growth, differentiation, proliferation and/or maintenance of various tissues and organs. Specifically, the invention provides for methods for inducing formation of haematopoietic, gut, neuronal, brain and muscle tissues comprising administering to progenitor cells a composition comprising at least one protein which is a member of the Frazzled protein family. The proteins of the invention are useful in the treatment of various disorders associated with defects in cellular formation, growth, differentiation, proliferation and/or maintenance of a variety of adult and embryonic tissues and organs including, for example, haematopoietic, gut, neuronal, muscle, brain, lung, pancreas, liver, spleen, kidney, intestines and/or other tissues and organs. They are also useful in the modulation of cellular formation, growth, differentiation, proliferation and/or maintenance of a variety of adult and embryonic tissues and organs. These proteins are also useful for augmenting the activity of other tissue and organ regenerating and differentiation factors.

In preferred embodiments, the compositions useful in these methods may comprise a protein having the amino acid sequence of SEQ ID NO 2, 4 and/or 6, as well as a protein comprising the amino acid sequence of SEQ ID NO 13, 14, 15, 16 17, and/or 18. In one embodiment, the method comprises administering the composition to a patient in vivo. Alternatively, the method may comprise administering the composition to cells in vitro and recovering haematopoietic, gut, neuronal, brain and muscle tissues, which may subsequently be administered to a patient. The composition may further comprise a suitable carrier for administration.

In other embodiments, the present invention comprises vectors comprising the above DNA molecules in operative association with an expression control sequence therefor, as well as host cells transformed with these vectors. In yet other embodiments, the present invention comprises methods for producing purified Frazzled proteins, WG67-16, WG67-19 and WA628 and compositions containing the Frazzled proteins WG67-16, WG67-19 and WA628. These methods may comprise the steps of: culturing a host cell transformed with a DNA sequence encoding a Frazzled protein such as described above; and recovering and purifying said Frazzled protein from the culture medium. The present invention further comprises the purified Frazzled polypeptide produced by the above methods, as well as purified Frazzled polypeptides such as WG67-16, WG67-19 and WA628 comprising an amino acid sequence encoded by the above DNA sequences. The proteins of the present invention may comprise the amino acid sequences or portions thereof of SEQ ID NO 2, 4, 6, 13, 14, 15, 16, 17, and/or 18 or, Frazzled protein such as WG67-16, WG67-19 or WA628 having a molecular weight of about 30 to about 35 kD, said protein comprising the amino acid sequences or portions thereof of SEQ ID NO 2, 4, 6, 13, 14, 15, 16, 17, and/or 18 and having Frazzled protein activity.

DESCRIPTION OF SEQUENCES

SEQ ID NO 1 is the 2190 nucleotides sequence of WG67-16; the coding sequence is from #44 through #889.

SEQ ID NO 2 is the 281 amino acid sequence encoded by SEQ ID NO 1.

SEQ ID NO 3 is the 1140 nucleotide sequence WG67-19; the coding sequence is from nucleotide #8 through #850.

SEQ ID NO 4 is the 280 amino acid sequence encoded by SEQ ID NO 3.

SEQ ID NO 5 is the 1146 nucleotide sequence of WA628 the coding sequence is from nucleotide #80 through #967.

SEQ ID NO 6 is the 295 amino acid sequence encoded by SEQ ID NO5.

SEQ ID NO 7 is the 502 nucleotide sequence of WG67-SP.

SEQ ID NO 8 is an inserted recognition site.

SEQ ID NO 9 is an inserted recognition site.

SEQ ID NO 10 is an inserted recognition site.

SEQ ID NO 11 and 12 are nucleotide sequences of the primers used in the isolation of the nucleotide sequences of the invention. P1 SEQ ID NO:13 is a consensus amino acid sequence comprised by certain of the Frazzled proteins of the invention where the first Xaa equals Ala or Ser; the second Xaa equals Met or Leu; the third Xaa equals Tyr or Phe; and the fourth Xaa equals Ile or Val.

SEQ ID NO:14 is a consensus amino acid sequence comprised by certain of the Frazzled proteins of the invention where the first Xaa equals Ser or Ile and the second Xaa equals Asp or Lys.

SEQ ID NO:15–SEQ ID NO:17 are consensus amino acid sequences comprised by certain of the Frazzled proteins of the invention.

SEQ ID NO:18 is a consensus amino acid sequence comprised by certain of the Frazzled proteins of the invention where the first Xaa equals Lys or Arg and the second Xaa equals Asn or His.

DESCRIPTION OF THE DEPOSITS

Two plasmids, pWG67-16/CS2$^+$ and pWG67-16/pED6, containing the WG67-16 DNA coding sequence, were used to transform an E. coli strain which was deposited with the American Type Culture Collection, 10801 University Boulevard, Manassas, Va. 20110-2209 20852 on May 9, 1997. This deposit has been accorded the accession number ATCC 98432. This deposit meets the requirements of the Budapest Treaty.

A plasmid, pWG67-19, which contains the WG67-19 DNA coding sequence was used to transform an E. coli strain and was deposited with the American Type Culture Collection, 10801 University Boulevard, Manassas, Va. 20110-2209 on May 13, 1997. This deposit has been accorded the accession number ATCC 98434. This deposit meets the requirements of the Budapest Treaty.

A plasmid, pWA628-5, which contains the WA628 DNA coding sequence was used to transform E. coli strain and was deposited with the American Type Culture Collection, 10801 University Boulevard, Manassas, Va. 20110-2209 on May 9, 1997. This deposit has been accorded the accession number ATCC 98430. This deposit meets the requirements of the Budapest Treaty.

DETAILED DESCRIPTION OF THE INVENTION

As used herein, the term "Frazzled protein" refers to the Frazzled protein members which share sequence homology to the extracellular binding domains of the Frizzled protein family, including those encoded by the genes Hfz3, Hfz5, and Hfz7, as well as other Frazzled proteins, and Frazzled protein members found in other species and which share sequence homology to Frizzled proteins from other species, such as those described in Wang et al., Wang et al., J. Biol. Chem., 271:4468–4476 (1996). Specific members of the Frazzled protein family include the WG67-16, WG67-19 and WA628 proteins, having the amino acid sequences as specified in SEQ ID NO 2, 4, and/or 6 and/or SEQ ID NO 13–18, as well as homologues of these proteins found in other species. Frazzled family proteins also exist in other species, including family members in Drosophila, Xenopus, C. elegans, zebrafish, as well as in rats, mice and humans. "Frazzled proteins" also include variants of the Frazzled proteins, such as allelic variants or variants induced by mutagenesis or deletions, and fragments of Frazzled or Frazzled proteins which variants and fragments retain Frazzled activity, e.g., such as, the ability to bind to proteins, such as the Wnt or Wnt-like proteins (which Wnt or Wnt-like proteins would otherwise bind to membrane bound receptors, such as the Frizzled proteins).

As used herein, the term "Frazzled activity" refers to one or more of the activities which are exhibited by the Frazzled proteins of the present invention e.g., including, but not limited to the proteins WG67-16, WG67-19, and WA628. In particular, "Frazzled activity" can include the ability to bind to Wnt or Wnt-like proteins, and can include the ability to regulate the binding of Wnt or Wnt-like proteins to receptors such as the Frizzled protein receptors. One such Wnt binding assay is described in Bhanot, Nature 382:225(1996). Briefly, cells transfected with a sequence encoding a protein having Frazzled activity are incubated with conditioned medium containing a Wnt or Wnt-like protein. Bound Wnt protein is visualized, e.g., following incubation with anti-Wnt antibody, e.g., a flourescent antibody.

"Frazzled activity" further includes the ability to regulate the formation, differentiation, proliferation and/or maintenance of cells and/or tissue, including for example connective tissue, organs and wound healing. In particular, "Frazzled activity" includes the ability to enhance and/or inhibit the formation, growth, proliferation, differentiation and/or maintenance of haematopoietic, gut, neuronal, pancreatic, cartilage, brain and muscle (both skeletal and cardiac) tissues. "Frazzled activity" also includes the activities of Frazzled proteins in the assays described in the examples herein.

The present invention also includes protein variants and functional fragments of the amino acid sequence of the Frazzled WG67-16, WG67-19 and WA628 proteins shown in SEQ ID NO 2, 4 and/or 6, and/or SEQ ID NO 13, 14, 15, 16 17, and/or 18, which retain Frazzled activity. The present invention also includes antibodies to a purified Frazzled protein such as WG67-16, WG67-19, and WA628 described above. The compositions of the present invention comprise a therapeutic amount of Frazzled protein such as one or more of the above Frazzled WG67-16, WG67-19 and WA628 proteins. Moreover, therapeutic compositions comprise effective combinations of Frazzled and Wnt and/or Wnt-like proteins.

It is expected that WG67-16, WG67-19 and WA628 protein, as expressed by mammalian cells such as CHO cells, exist as a heterogeneous population of active species of WG67-16, WG67-19 and WA628 protein with varying N-termini. Based in part upon the Von Heginje signal peptide prediction algorithm, the first 15 to 18 amino acids of WG67 and the first 24 to 26 amino acids of WA628 appear to be involved in signaling for the secretion of the mature peptide. It is expected that active species may optionally include a signal peptide and that the DNA sequences encoding active WG67-16, WG67-19, and WA628 proteins may include those DNA sequences encoding a signal peptide region(s).

In yet another embodiment, the present invention comprises a method of altering the regulation of genes comprising administering an effective amount of the above compositions. For example, the alteration of regulation of pancreatic genes may be accomplished by stimulating or inhibiting binding by Wnt proteins of receptor proteins, for example, binding between the Frazzled WG67-16, WG67-19 and WA628 protein of the present invention and the Wnt protein. Thus, the Frazzled protein family, including WG67-16, WG67-19 and WA628, can regulate the binding interaction of Wnt genes with receptor proteins, such as the Frizzled receptor proteins.

The present invention also encompasses hybrid or fusion vectors comprising the coding DNA sequences of the present invention and other Frazzled encoding sequences, linked to a tissue specific sequence or inducible regulatory sequence, such as a promoter or operator. In a preferred embodiment of the invention, the coding sequence for Frazzled WG67- 16, WG67-19 and WA628 protein is operably linked to one or more promoters, enhancers and/or other regulatory elements from genes which are selectively expressed in haematopoietic, gut, neuronal, brain and muscle tissues or in chrondocyte cells and/or cartilage tissues. For example, the collagen type II enhancer promoter, which is known to be expressed in cartilage during mesenchymal condensation and cartilage. Metsaranta et al., Dev. Dynamics, 204:202–210 (1996); Li et al., Genes Develop., 9:2821–2830 (1996). Another regulatory element useful in the present invention is the tenascin C promoter. Tenascin C is expressed in articular cartilage. Pacifici et al., Matrix Biol., 14:689–698 (1996). Additionally, the DNA sequence encoding Frazzled proteins such as WG67-16, WG67-19 and WA628 may be operatively linked to one or more regulatory sequences from proteoglycan core proteins, which are selectively produced in chondrocytes and/or cartilage tissue. In other preferred embodiments of the invention, the coding sequences for Frazzled proteins, such as WG67-16, WG67-19 and WA628 protein, are operably linked to the promoter isolated from the IDX gene. This promoter is selectively expressed in pancreatic cells and tissue. Thus, a hybrid DNA vector in which the IDX promoter is operably linked to a DNA sequence encoding a Frazzled protein such as WG67-16, WG67-19 and WA628 protein is useful for selective expression of the protein in pancreatic tissue, for example for the treatment of a pancreatic disorder or for altering the regulation of pancreatic genes, for example by stimulating or inhibiting binding by Wnt proteins of its receptor protein, for example by binding between the expressed Frazzled proteins such as WG67-16, WG67-19 and WA628 protein and the Wnt protein. Vectors using other tissue-selective regulatory elements and inducible regulatory elements may also be useful for the selective or inducible expression of the Frazzled proteins such as WG67-16, WG67-19 and WA628 proteins of the present invention.

Another aspect of the invention provides pharmaceutical compositions containing a therapeutically effective amount of a Frazzled protein, such as rat or human Frazzled WG67-16, WG67-19 and WA628 protein, in a pharmaceutically acceptable vehicle or carrier. These compositions of the invention may be used to induce expression of factors in and/or differentiation of a variety of adult and embryonic tissues and organs, and particularly, to induce formation, growth, differentiation, proliferation and/or maintenance of various tissues and organs and may be used in the formation of haematopoietic, gut, neuronal, brain and muscle tissues and chondrocytes and/or cartilage tissue phenotype. These compositions may further be utilized in order to enhance and/or to inhibit the formation, growth, proliferation, differentiation and/or maintenance of beta cells, and other cell types typically found in the islets of Langerhans or other pancreatic cells, as well a variety of adult and embryonic tissues and organs including, for example, haematopoietic, gut, neuronal, muscle, brain, lung, pancreas, liver, spleen, kidney, intestines and/or other tissues and organs. They are useful in the treatment of various disorders associated with defects in cellular formation growth, differentiation, proliferation and/or maintenance of a variety of adult and embryonic tissues and organs including, for example, brain, lung, pancreas, liver, spleen, kidney, intestines and/or other tissues and organs. The compositions comprising Frazzled protein members such as WG67-16, WG67-19 and WA628 protein may be used to treat precursor or stem cells, such as pancreatic stem cells, which are able to differentiate into cells which comprise differentiated tissue or organs, such as pancreatic cells, in order to enhance the formation, differentiation, proliferation and/or maintenance of such cells, tissue or organs. Methods for forming and maintaining such cells are described, for example, in WO93/00441, the disclosure of which is incorporated herein by reference.

The compositions of the invention may comprise, in addition to a Frazzled protein member, such as WG67-16, WG67-19 and WA628 protein, other therapeutically useful agents including growth factors such as epidermal growth factor (EGF), fibroblast growth factor (FGF), transforming growth factor (TGF-α and TGF-β, activins, inhibins, bone morphogenetic proteins (BMP), Wnt proteins, and insulin-like growth factor (IGF). The compositions may also include an appropriate matrix for instance, for supporting the composition and providing a surface for chondrocytic cell, and/or cartilaginous tissue growth. The matrix may provide slow release of the Frazzled WG67-16, WG67-19 and WA628 protein and/or the appropriate environment for presentation thereof.

The Frazzled protein member, such as WG67-16, WG67-19 and WA628 protein, containing compositions may be employed in methods for treating a number of tissue defects, and healing and maintenance of various types of tissues and wounds. The tissues and wounds which may be treated include cartilage, but may also include epidermis, nerve, muscle, cardiac muscle, connective tissue, such as bone, tendon and ligament and other tissues and wounds, and a variety of adult and embryonic tissues and organs including, for example, haematopoietic, gut, neuronal, muscle, brain, lung, pancreas, liver, spleen, kidney, intestines and/or other tissues and organs. These methods, according to the invention, entail administering an effective amount of a Frazzled protein member such as WG67-16, WG67-19 and WA628 protein. The Frazzled protein WG67-16, WG67-19 and WA628 containing compositions may also be used to treat or prevent such conditions as rheumatoid arthritis, osteoarthritis, and other abnormalities of cartilaginous tissues, or other conditions associated with other organs or tissues, such as pancreas, liver, spleen, lung, cardiac, brain, and kidney tissue, and other tissues and organs. These methods may also entail the administration of a protein of the invention in conjunction with administration of at least one other protein, for example growth factors including EGF, FGF, TGF-α, TGF-β, BMP, activin, inhibin and IGF.

Still a further aspect of the invention are DNA sequences coding for expression of a Frazzled protein member such as WG67-16, WG67-19 and WA628 protein. Such sequences include the sequence of nucleotides in a 5' to 3' direction illustrated in SEQ ID NO 1, 3, 5, and/or 7, DNA sequences which, but for the degeneracy of the genetic code, are identical to these DNA sequences and which encode proteins comprising amino acid sequences of SEQ ID NOs.: 2, 4, 6, 13, 14, 15, 16, 17, and/or 18. Further included in the present invention are DNA sequences which hybridize under stringent conditions with the DNA sequences of SEQ ID Nos.: 1, 3, 5, and/or 7 and encode a protein having the ability to bind to one or more Wnt proteins, and/or which have the ability to enhance and/or inhibit the formation, growth, proliferation, differentiation, maintenance of pancreatic cells, such as insulin-producing beta cells, or a variety of adult and embryonic tissues and organs including, for example, haematopoietic, gut, neuronal, muscle, brain, lung, liver, spleen, kidney, intestines and/or other tissues and organs. Preferred DNA sequences include those which hybridize under stringent conditions (see, T. Maniatis et al, Molecular Cloning (A Laboratory Manual), Cold Spring Harbor Laboratory (1982), pages 387 to 389). It is generally preferred that such DNA sequences encode a polypeptide which is at least about 80% homologous, and more preferably at least about 90% homologous, to the amino acid sequences of SEQ ID NO 2, 4, and/or 6. Also preferred are DNA sequences having greater than 80% homology to SEQ ID NO 13 and/or 14; also preferred are DNA sequences having greater than or equal to 80% homology to SEQ ID NO 15, 16, 17, and/or 18. Finally, allelic or other variations of the sequences of SEQ ID NO 1, 3, 5, and/or 7, whether such nucleotide changes result in changes in the peptide sequence, and where the peptide sequence still retains Frazzled activity, are also included in the present invention. The present invention also includes functional fragments of the DNA sequences encoding Frazzled protein family members such as WG67-16, WG67-19 and WA628 proteins of SEQ ID NO 2, 4 and/or 6 which encode a polypeptide which retains the activity of Frazzled protein. The determination whether a particular variant or fragment of a Frazzled protein family member such as WG67-16, WG67-19 and WA628 protein of the present invention, such as those shown in SEQ ID NO 2, 4 and/or 6 retain Frazzled activity, is routinely performed using the assays described in the examples herein.

The DNA sequences of the present invention are also useful, for example, as probes for the detection of mRNA encoding other Frazzled protein in a given cell population. The DNA sequences may also be useful for preparing vectors for gene therapy applications as described below.

A further aspect of the invention includes vectors comprising a DNA sequence as described above in operative association with an expression control sequence therefor. These vectors may be employed in a novel process for producing a recombinant Frazzled protein family member such as WG67-16, WG67-19 and WA628 protein of the invention in which a cell line transformed with a DNA sequence encoding a Frazzled protein family member such as WG67-16, WG67-19 and WA628 protein in operative association with an expression control sequence therefor, is cultured in a suitable culture medium and a Frazzled family protein is recovered and purified therefrom. This process may employ a number of known cells both prokaryotic and eukaryotic as host cells for expression of the polypeptide. The vectors may also be used in gene therapy applications. In such use, the vectors may be transfected into the cells of a patient ex vivo, and the cells may be reintroduced into a patient. Alternatively, the vectors may be introduced into a patient in vivo through targeted transfection.

In a preferred embodiment of the invention, vectors are prepared using one or more native and/or non-native regulatory elements, such as promoters and/or enhancers operatively associated with the coding sequence for Frazzled WG67-16, WG67-19, and WA628, in order to achieve expression of Frazzled WG67-16, WG67-19 and WA628 in a desired cell tissue and/or at a desired time in development. For example, a vector may be constructed using the promoter element from the well-characterized IDX gene, which is known to be constitutively expressed in pancreatic cells, including beta cells, during development. By operatively associating the promoter from the IDX gene with the coding sequence for Frazzled, and transforming suitable cells, such as pancreatic stem cells as described in WO93/00441, one can express Frazzled WG67-16, WG67-19 and WA628 in these cells, thus promoting the desired effects of formation, growth, proliferation, differentiation and/or maintenance of cells such as pancreatic beta cells which are able to secrete insulin, either in in vitro culture or in vivo.

Still a further aspect of the invention are Frazzled protein family members such as WG67-16, WG67-19 and WA628 proteins or polypeptides. Such polypeptides are characterized by having an amino acid sequence comprising a sequence of SEQ ID NOs.: 2, 4, 6, 13, 14, 15, 16, 17, and/or 18, variants of these amino acid sequences, including naturally occurring allelic variants, and other variants in which the protein retains Frazzled activity for example, the ability to enhance and/or inhibit the formation, growth, proliferation, differentiation and/or maintenance of haematopoietic, gut, neuronal, brain and muscle tissues and of chondrocytes and/or cartilage tissue and/or pancreatic or other organ tissue, such as haematopoietic, gut, neuronal, muscle, liver, spleen, lung, cardiac, brain and kidney tissue, characteristic of Frazzled protein. Preferred polypeptides include a polypeptide which is at least about 80% homologous, and more preferably at least about 90% homologous to a Frazzled protein family member such as WG67-16, WG67-19 and WA628 amino acid sequences of SEQ ID NO 2, 4, and/or 6. Finally, allelic or other variations of the sequences of SEQ ID NOs.: 2, 4, and/or 6, whether such amino acid changes are induced by mutagenesis, chemical alteration, or by alteration of DNA sequence used to produce the polypeptide, where the peptide sequence still has Frazzled activity, are also included in the present invention. The present invention also includes fragments of the amino acid sequence of Frazzled protein family members WG67-16, WG67-19 and WA628 of SEQ ID NO 2, 4, and/or 6, which retain the activity of Frazzled protein. One skilled in the art can readily produce such variations and fragments of the Frazzled WG67-16, WG67-19 and WA628 protein using techniques known in the art, and can readily assay them for activity, as described in the examples and specification herein.

The purified proteins of the present inventions may be used to generate antibodies, either monoclonal or polyclonal, to Frazzled protein family members such as WG67-16, WG67-19 and WA628 proteins and/or other related proteins, using methods that are known in the art of antibody production. Thus, the present invention also includes antibodies to human Frazzled proteins. The antibodies can be used for purification of Frazzled proteins WG67-16, WG67-19 and WA628 or for inhibiting or preventing the effects of Frazzled proteins either in vitro or in vivo. The Frazzled proteins WG67-16, WG67-19 and WA628 are useful for inducing the growth and/or differentiation of embryonic cells and/or stem cells. Thus, the proteins or compositions of the present invention are also be useful for treating cell populations, such as embryonic cells or stem cell populations, to enhance, enrich or to inhibit the growth and/or differentiation of the cells. For example, the Frazzled proteins WG67-16, WG67-19 and WA628 are useful for treating cell populations to enhance and/or inhibit the formation, differentiation, proliferation and/or maintenance of chondrocytes, cartilaginous tissue, other connective tissues and/or other cells such as cells of pancreatic origin, or a variety of adult and embryonic tissues and organs including, for example, haematopoietic, gut, neuronal, muscle, brain, lung, pancreas, liver, spleen, kidney, intestines and/or other tissues and organs. The treated cell populations are useful for, among other things, gene therapy applications, as described below.

It is of particular interest that the frazzled genes for WG67-16, WG67-19 and WA628 appear to encode secreted factors, thus providing soluble receptors capable of binding with Wnt and Wnt-like proteins, and thereby initiating and/or blocking signal transduction by Wnt proteins. Thus, the frazzled gene family, including WG67-16, WG67-19 and WA628, are capable of regulating the binding interaction of Wnt genes to receptor proteins, such as the Frizzled receptor proteins. The potential signal transduction regulation activities of these proteins, along with the presence and/or expression of wnt genes in pancreas and other organs and tissues suggests that the Frazzled proteins such as WG67-16, WG67-19 and WA628 are important regulators of differentiation of tissue and organs, and are involved in the induction, formation, growth, differentiation, proliferation and/or maintenance of tissues and organs. Thus, the proteins of the present invention may be useful in wound healing, tissue and organ repair and regeneration processes, as well as in differentiation of tissue, for example in embryonic development. In particular, the Frazzled proteins WG67-16, WG67-19 and WA628 may be useful for the induction, formation, growth, differentiation, proliferation and/or maintenance and repair of haematopoietic, gut, neuronal, brain and muscle tissues and of chondrocytes and/or cartilage tissue. Thus, these proteins, and compositions containing them, may be useful in the treatment of cartilage disorders, such as osteoarthritis, rheumatoid arthritis and articular cartilage defects, and in the enhancement and/or inhibition of cellular formation, growth, differentiation, proliferation and/or maintenance, for example formation of chondrocytes and/or cartilage tissue.

The Frazzled proteins provided herein include factors encoded by DNA sequences similar to those of SEQ ID NO 1, 3, 5, and/or 7, but into which modifications or deletions are naturally provided (e.g., allelic variations in the nucleotide sequence which may result in amino acid changes in the polypeptide) or deliberately engineered. For example, synthetic polypeptides may wholly or partially duplicate continuous sequences of the amino acid residues of SEQ ID NO 2, 4, and/or 6. These sequences, by virtue of sharing primary, secondary, or tertiary structural and conformational characteristics with Frazzled polypeptides, such as WG67-16, WG67-19 and WA628, may possess biological properties in common therewith. Thus, these modifications and deletions of the native Frazzled polypeptides may be employed as biologically active substitutes for naturally-occurring Frazzled polypeptides in therapeutic processes. It can be readily determined whether a given variant or fragment of a Frazzled WG67-16, WG67-19 and WA628 maintains the biological activity of Frazzled by subjecting both a Frazzled and the variant or fragment of a Frazzled to a Frazzled activity assay. For example, the variant or fragment may be used in a competitive binding assay to test for binding to the Wnt gene, or to test for binding to Wnt or a Wnt-like protein.

Other specific mutations of the sequences of Frazzled proteins WG67-16, WG67-19 and WA628 described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Such variants of Frazzled WG67-16, WG67-19 and WA628 are within the present invention. Additionally, bacterial expression of Frazzled proteins will result in production of a non-glycosylated protein, even if the glycosylation sites are left unmodified. Such bacterially produced versions of Frazzled WG67-16, WG67-19 and WA628 are within the present invention.

The present invention also encompasses the novel DNA sequences, free of association with DNA sequences encoding other proteinaceous materials, and coding for expression of Frazzled proteins, such as WG67-16, WG67-19 and WA628. These DNA sequences include those depicted in SEQ ID NOs.: 1, 3, 5, and/or 7 in a 5' to 3' direction, as well as nucleotide sequences which include the concensus amino acid sequences of SEQ ID NO 15, 16, 17, and/or 18, and those sequences which hybridize thereto under stringent hybridization conditions (for example, 0.1X SSC, 0.1% SDS at 65° C.; see, T. Maniatis et al, Molecular Cloning (A Laboratory Manual), Cold Spring Harbor Laboratory (1982), pages 387 to 389) and encode a protein having Frazzled activity. As used herein, the term "stringent hybridization conditions" refers to the use of initial low stringency hybridization conditions (such as 6X SSC, 0.5% SDS, at about 60° C.), overnight which is followed by a higher stringency wash condition (such as 2XSSC, 0.1% SDS, at about 20° C.) or an even higher stringency wash (such as 0.1XSSC, 0.1% SDS, at about 65° C., for less than an hour).

Similarly, DNA sequences which code for Frazzled proteins WG67-16, WG67-19 and WA628 coded for by the sequences of SEQ ID NO 1, 3, 5, and/or 7, or Frazzled proteins or WG67-16, WG67-19 and WA628 which comprise the amino acid sequences of SEQ ID NO 2, 4, 6, and/or SEQ ID NO 15, 16, 17, and/or 18, but which differ in codon sequence due to the degeneracies of the genetic code or allelic variations (naturally-occurring base changes in the species population which may or may not result in an amino acid change) also encode the novel factors described herein. Variations in the DNA sequences of SEQ ID NO 1, 3, 5, and/or 7 which are caused by point mutations or by induced modifications (including insertion, deletion, and substitution) to enhance the activity, half-life or production of the polypeptides encoded are also encompassed in the invention.

Another aspect of the present invention provides a novel method for producing Frazzled proteins such as WG67-16, WG67-19 and WA628. The method of the present invention involves culturing a suitable cell line, which has been transformed with a DNA sequence encoding a Frazzled protein, such as WG67-16, WG67-19 and WA628 of the invention, under the control of known regulatory sequences. The transformed host cells are cultured and the Frazzled proteins, such as WG67-16, WG67-19 and WA628 are recovered and purified from the culture medium. The purified proteins are substantially free from other proteins with which they are co-produced as well as from other contaminants. Alternatively, a suitable cell line(s) can be co-transfected with sequences encoding Frazzled and encoding Wnt, or a Wnt-like protein, either on separate or single vectors. The resultant expression product(s) can be purified as separate and/or complexes of Frazzled and Wnt and/or Wnt-like protein(s).

Suitable cells or cell lines may be mammalian cells, such as Chinese hamster ovary cells (CHO). The selection of suitable mammalian host cells and methods for transformation, culture, amplification, screening, product production and purification are known in the art. See, e.g., Gething and Sambrook, Nature, 293:620–625 (1981), or alternatively, Kaufman et al, Mol. Cell. Biol., 5(7):1750–1759 (1985) or Howley et al, U.S. Pat. No. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of E. coli (e.g., HB101, MC1061) are well-known as host cells in the field of biotechnology. Various strains of B. subtilis, Pseudomonas, other bacilli and the like may also be employed in this method. For expression of the protein in bacterial cells, DNA encoding the propeptide signal peptide of Frazzled is generally not necessary.

Many strains of yeast cells, known to those skilled in the art, can be used as host cells for expression of the polypeptides of the present invention. Additionally, where desired, insect cells may be utilized as host cells in the method of the present invention. See, e.g., Miller et al, Genetic Engineering, 8:277–298 (Plenum Press 1986) and references cited therein.

Another aspect of the present invention provides vectors for use in the method of expression of Frazzled polypeptides, such as WG67-16, WG67-19 and WA628. Preferably the vectors contain the full novel DNA sequences described above which encode the novel factors of the invention. Additionally, the vectors contain appropriate expression control sequences permitting expression of the Frazzled protein sequences. Alternatively, vectors incorporating modified sequences as described above are also embodiments of the present invention. Additionally, the sequence of SEQ ID NO 1, 3, 5, and/or 7, or other sequences encoding Frazzled proteins, such as WG67-16, WG67-19 and WA628, can be manipulated to express a mature Frazzled protein, such as WG67-16, WG67-19 and WA628, by deleting Frazzled propeptide signal peptide sequences and replacing them with sequences encoding the propeptide signal peptides of other Frazzled proteins or other suitable propeptides. Thus, the present invention includes chimeric DNA molecules encoding a propeptide signal peptide from a member of the Frazzled family linked in correct reading frame to a DNA sequence encoding a Frazzled protein, such as WG67-16, WG67-19 and WA628 polypeptide. The sequences can also be suitably configured to generic multimeric forms including homodimers and heterodimers and the like.

The vectors may be employed in the method of transforming cell lines and contain selected regulatory sequences in operative association with the DNA coding sequences of the invention which are capable of directing the replication and expression thereof in selected host cells. Regulatory sequences for such vectors are known to those skilled in the art and may be selected depending upon the host cells. Such selection is routine and does not form part of the present invention.

In order to produce rat, human or other mammalian Frazzled proteins, the DNA encoding it is transferred into an appropriate expression vector and introduced into mammalian cells or other preferred eukaryotic or prokaryotic hosts by conventional genetic engineering techniques. The preferred expression system for biologically active recombinant human Frazzled is contemplated to be stably transformed mammalian cells.

One skilled in the art can construct mammalian expression vectors by employing the sequence of SEQ ID NO 1, 3, 5, and/or 7, or other DNA sequences encoding Frazzled proteins or other modified sequences and known vectors, such as pCD (Okayama et al., Mol. Cell Biol., 2:161–170 (1982)), pJL3, pJL4 (Gough et al., EMBO J., 4:645–653 (1985)) and pMT2 CXM.

The mammalian expression vector pMT2 CXM is a derivative of p91023(b) (Wong et al., Science 228:810–815, 1985) differing from the latter in that it contains the ampicillin resistance gene in place of the tetracycline resistance gene and further contains a XhoI site for insertion of cDNA clones. The functional elements of pMT2 CXM have been described (Kaufman, R. J., 1985, Proc. Natl. Acad. Sci. USA 82:689–693) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in E. coli.

Plasmid pMT2 CXM is obtained by EcoRi digestion of pMT2-VWF, which has been deposited with the American Type Culture Collection (ATCC), Rockville, Md. (USA) under accession number ATCC 67122. EcoRi digestion excises the cDNA insert present in pMT2-VWF, yielding pMT2 in linear form which can be ligated and used to transform E. coli HB 101 or DH-5 to ampicillin resistance. Plasmid pMT2 DNA can be prepared by conventional methods. pMT2 CXM is then constructed using loopout/in mutagenesis (Morinaga, et al., Biotechnology 84: 636 (1984). This removes bases 1075 to 1145 relative to the Hind III site near the SV40 origin of replication and enhancer sequences of pMT2. In addition it inserts the following sequence:

SEQ ID NO 8: 5'PO-CATGGGCAGCTCGAG-3' at nucleotide 1145. This sequence contains the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

pEMC2β1 derived from pMT21 may also be suitable in practice of the invention. pMT21 is derived from pMT2 which is derived from pMT2-VWF. As described above EcoRI digestion excises the cDNA insert present in pMT-VWF, yielding pMT2 in linear form which can be ligated and used to transform E. Coli HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR:

SEQ ID NO 9: 5'-CTGCAGGCGAGCCTGAATTCCTCGAGCCAT-CATG-3'

PstI Eco RI XhoI

Second, a unique ClaI site is introduced by digestion with EcoRV and XbaI, treatment with Klenow fragment of DNA polymerase I, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B 1.

A portion of the EMCV leader is obtained from pMT2-ECAT1 (S. K. Jung, et al, J. Virol 63:1651–1660 (1989)) by digestion with Eco RI and PstI, resulting in a 2752 bp fragment. This fragment is digested with TaqI yielding an Eco RI-TaqI fragment of 508 bp which is purified by electrophoresis on low melting agarose gel. A 68 bp adapter and its complementary strand are synthesized with a 5' TaqI protruding end and a 3' XhoI protruding end which has the following sequence:

SEQ ID NO 10: 5'CGAGGTTAAAAAACGTCTAGGC-CCCCCGAACCACGGGGACGTGGTTT

TaqI

TCCTTTGAAAAACACGATTGC-3'

XhoI

This sequence matches the EMC virus leader sequence from nucleotide 763 to 827. It also changes the ATG at position 10 within the EMC virus leader to an ATT and is followed by a XhoI site. A three way ligation of the pMT21 Eco RI-XhoI fragment, the EMC virus EcoRI-TaqI fragment, and the 68 bp oligonucleotide adapter TaqI-XhoI adapter resulting in the vector pEMC2β1 . This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells.

The construction of vectors may involve modification of the Frazzled WG67-16, WG67-19 and WA628 DNA sequences. For instance, Frazzled WG67-16, WG67-19 and WA628 cDNA can be modified by removing the non-coding nucleotides on the 5' and 3' ends of the coding region. The deleted non-coding nucleotides may or may not be replaced by other sequences known to be beneficial, e.g., for expression. These vectors are transformed into appropriate host cells for expression of Frazzleds, such as WG67- 16, WG67-19 and WA628 proteins. Additionally, the sequences of SEQ ID NO 1, 3, 5, and/or 7 or other sequences encoding Frazzled proteins can be manipulated to express a mature Frazzled protein member such as WG67-16, WG67-19 and WA628 protein by deleting Frazzled WG67-16, WG67-19 and WA628 encoding propeptide signal peptide sequences and replacing them with sequences encoding the complete propeptides signal peptides of other proteins.

One skilled in the art can manipulate the sequences of SEQ ID NO 1, 3, 5, and/or 7 by eliminating or replacing the mammalian regulatory sequences flanking the coding sequence with bacterial sequences to create bacterial vectors for intracellular or extracellular expression by bacterial cells. For example, the coding sequences could be further manipulated (e.g., ligated to other known linkers or modified by deleting non-coding sequences therefrom or altering nucleotides therein by other known techniques). The modified Frazzled protein family member such as WG67-16, WG67-19 and WA628 coding sequence could then be inserted into a known bacterial vector using procedures such as described in T. Taniguchi et al., Proc. Natl Acad. Sci. USA, 77:5230–5233 (1980). This exemplary bacterial vector could then be transformed into bacterial host cells and a protein expressed thereby. For a strategy for producing extracellular expression of Frazzled, such as WG67-16, WG67-19 and WA628, proteins in bacterial cells, see, e.g., European patent application EPA 177,343. In addition, the Frazzled proteins of the invention, and Frazzled/Wnt complexes can be expressed as a thioredoxin fusion as is known to those skilled in the art and as is described in U.S. Pat. No. 5,646,016 and published in WO 95/16044; Jun. 15, 1995.

Similar manipulations can be performed for the construction of an insect vector (See, e.g., procedures described in published European patent application 155,476) for expression in insect cells. A yeast vector could also be constructed employing yeast regulatory sequences for intracellular or extracellular expression of the factors of the present invention by yeast cells. (See, e.g., procedures described in published PCT application WO86100639 and European patent application EPA 123,289).

A method for producing high levels of a Frazzled protein such as WG67-16, WG67-19 and WA628 protein of the invention in mammalian cells can involve the construction of cells containing multiple copies of the heterologous Frazzled gene such as the WG67-16, WG67-19 and WA628 genes. The heterologous gene is linked to an amplifiable marker, e.g., the dihydrofolate reductase (DHFR) gene for which cells containing increased gene copies can be selected for propagation in increasing concentrations of methotrexate (MTX) according to the procedures of Kaufman and Sharp, J. Mol. Biol., 159:601–629 (1982). This approach can be employed with a number of different cell types.

For example, a plasmid containing a DNA sequence for a Frazzled family member WG67-16, WG67-19 and WA628 of the invention in operative association with other plasmid sequences enabling expression thereof and the DHFR expression plasmid pAdA26SV(A)3 (Kaufman and Sharp, Mol. Cell. Biol., 2:1304 (1982)) can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g., sequential steps in 0.02, 0.2, 1.0 and 5 uM MTX) as described in Kaufman et al., Mol Cell Biol., 5:1750 (1983). Transformants are cloned, and biologically active Frazzled WG67-16, WG67-19 and WA628 expression is monitored by assay in one of the assays described in the examples below. Frazzled protein expression increases with increasing levels of MTX resistance. Frazzled polypeptides are characterized using standard techniques known in the art such as pulse labeling with 35S methionine or cysteine and polyacrylamide gel electrophoresis. Similar procedures can be followed to produce other related Frazzled proteins.

A protein of the present invention, which demonstrates Frazzled activity, has application in the induction, formation, growth, differentiation, proliferation and/or maintenance and healing of cells and tissues such as haematopoietic, gut, neuronal, brain and muscle tissues or, chondrocytes and/or cartilaginous tissue, as well as pancreatic tissue, and other organ tissues, in humans and other animals. Such a preparation employing a Frazzled protein may have prophylactic use in treatment of rheumatoid arthritis and osteoarthritis and traumatic injury to cartilage, as well as preventing pancreatic tumors, diabetes and other pancreatic tissue disorders. De novo formation of beta cells, islet of Langerhans cells, and other cells of pancreatic phenotype, induced by a Frazzled protein contributes to the repair of congenital, trauma induced, or oncologic tissue defects or conditions. A Frazzled, such as WG67-16, WG67-19 and WA628, protein may also be used in the treatment of pancreatic disease, and in other tissue and organ repair processes. Such agents may provide an environment to attract suitable stem cells, stimulate growth and proliferation of pancreas-forming cells or induce differentiation of progenitors of pancreas-forming cells, and may also support the regeneration of other tissues and organs. Frazzled polypeptides of the invention may also be useful in the treatment of organ disorders such as pancreitis or diabetes.

The proteins of the invention may also be used in wound healing and in related tissue repair. The types of wounds include, but are not limited to burns, incisions and ulcers. (See, e.g., PCT Publication WO84/01106 for discussion of wound healing and related tissue repair). It is further contemplated that proteins of the invention may increase neuronal, astrocytic and/or glial cell survival and therefore be useful in transplantation and treatment of conditions exhibiting a decrease in neuronal survival and repair. The proteins of the invention may further be useful for the treatment of conditions related to other types of tissue, such as nerve, epidermis, muscle, connective tissue, such as bone, cartilage, tendon and ligament, and other tissues such as haematopoietic, gut, neuronal, brain and muscle tissues and pancreas, liver, spleen, lung, cardiac, brain and kidney tissue. The proteins of the present invention may also have value as a dietary supplement, or as additives for cell culture media. For this use, the proteins may be used in intact form, or may be predigested to provide a more readily absorbed supplement.

The proteins of the invention may also have other useful properties characteristic of the Frazzled family of proteins. Such properties include angiogenic, chemotactic and/or chemoattractant properties, and effects on cells including differentiation responses, cell proliferative responses and responses involving cell adhesion, migration and extracellular matrices. These properties make the proteins of the invention potential agents for wound healing, reduction of fibrosis and reduction of scar tissue formation. The proteins of the invention may also be useful for the induction of formation of cells capable of secreting valuable hormones, such as insulin, glucagon, or other endocrine or exocrine hormones.

A further aspect of the invention is a therapeutic method and composition for treating disorders of cartilage and connective tissue, as well as disorders of the pancreas, diabetes, and other conditions related to pancreatic tissue disorders or diseases. The invention further comprises therapeutic methods and compositions for wound healing and tissue repair. Such compositions comprise a therapeutically effective amount of at least one Frazzled protein of the present invention in admixture with a pharmaceutically acceptable vehicle, carrier or matrix. It is further contemplated that compositions of the invention may increase neuronal and glial cell survival and therefore be useful in transplantation and treatment of conditions exhibiting a decrease in neuronal survival.

It is expected that the proteins of the invention may act in concert with or perhaps synergistically with other related proteins and growth factors. Further therapeutic methods and compositions of the invention therefore comprise a therapeutic amount of at least one Frazzled protein of the invention with a therapeutic amount of at least one other protein, such as a member of the TGF-β superfamily of proteins, which includes the bone morphogenetic proteins (BMPs), growth and differentiation factors (GDFs) and other proteins. The composition may include other agents and growth factors such as epidermal growth factor (EGF), fibroblast growth factor (FGF), platelet derived growth factor (PDGF), transforming growth factors (TGF-α and TGF-β), activins, inhibins, and β-fibroblast growth factor (βFGF), parathyroid hormone (PTH), leukemia inhibitory factor (LIF/HILDA/DIA), insulin-like growth factors (IGF-I and IGF-II) and Wnt proteins. Portions of these agents may also be used in compositions of the present invention.

The preparation and formulation of such physiologically acceptable protein compositions, having due regard to pH, isotonicity, stability and the like, is within the skill of the art. The therapeutic compositions are also presently valuable for veterinary applications due to the lack of species specificity in Frazzled proteins. Particularly domestic animals and thoroughbred horses in addition to humans are desired patients for such treatment with the Frazzled proteins of the present invention.

The therapeutic method includes administering the composition topically, systemically, or locally as by injection or implantation. When administered, the therapeutic composition for use in this invention is, of course, in a pyrogen-free, physiologically acceptable form. Further, the composition may desirably be encapsulated or injected in a viscous form for delivery to the tissue site. Topical administration may be suitable for wound healing and tissue repair. Therapeutically useful agents other than the Frazzled proteins which may also optionally be included in the composition as described above, may alternatively or additionally, be administered simultaneously or sequentially with the Frazzled composition in the methods of the invention.

For implantation, the composition preferably includes a matrix capable of delivering Frazzled WG67-16, WG67-19 and WA628 proteins to the site of pancreatic or other tissue damage, providing a structure for the developing tissue and optimally capable of being resorbed into the body. The matrix may provide slow release of Frazzled WG67-16, WG67-19 and WA628 and/or other protein, as well as proper presentation and appropriate environment for cellular infiltration. Such matrices may be formed of materials presently in use for other implanted medical applications. The choice of matrix material is based on biocompatibility, biodegradability, mechanical properties, cosmetic appearance and interface properties. The particular application of the Frazzled WG67-16, WG67-19 and WA628 compositions will define the appropriate formulation.

The dosage regimen will be determined by the attending physician considering various factors which modify the action of the Frazzled WG67-16, WG67-19 and WA628 protein, e.g., amount of tissue desired to be formed, the site of tissue damage, the condition of the damaged tissue, the size of a wound, type of damaged tissue, the patient's age, sex, and diet, the severity of any infection, time of administration and other clinical factors. The dosage may vary with the type of matrix used in the reconstitution and the types of Frazzled, such as WG67-16, WG67-19 and WA628 proteins in the composition. The addition of other known growth factors, such as IGF I (insulin like growth factor I), to the final composition, may also effect the dosage.

Progress can be monitored by periodic assessment of tissue growth and/or repair. The progress can be monitored, for example, x-rays, histomorphometric determinations and tetracycline labeling.

The following examples illustrate practice of the present invention in recovering, characterizing, and using Frazzled protein family members, such as WG67-16, WG67-19 and WA628 protein, and employing the DNA to recover human Frazzled and other Frazzled proteins, obtaining the human proteins and expressing the proteins via recombinant techniques.

EXAMPLE 1

Isolation of the Xenopus frazzled cDNAs by Hybridization

Xenopus WA628-5, WG67-16 and WG67-19 full-length cDNAs were isolated from a dT-primed cDNA library constructed in the plasmid vector CS2+. cDNA was made from Xenopus embryos (stage 11.5–12). The probe sequences used to isolate the clones for WA628 and WG67 were as follows:

SEQ ID NO 11:
5'-ATACATAGATTGCGAGCCACACGCCAA-3' and
SEQ ID NO 12:
5'-ACGCACTTGGTGGATAATCCAATGTCA-3',
respectively.

The DNA probes were radioactively labelled with 32P and used to screen the Xenopus dT-primed cDNA library, under high stringency hybridization/wash conditions, to identify clones containing sequences of the WA628 and WG67 genes.

Approximately 80,000 library transformants were plated at a density of approximately 4000 transformants per plate on selective plates to screen for WA628. Approximately 171,000 library transformants were plated at a density of approximately 3800 transformants per plate on selective plates to screen for WG67. Nitrocellulose replicas of the transformed colonies were hybridized to the 32P labelled DNA probe in standard hybridization buffer (6X SSC, 0.5% SDS, 5X Denhardt's, 10 mM EDTA, pH8, 100 mg/ml Bakers Yeast ribonucleic acid) under high stringency conditions (65° C. for 2 hours). After 2 hours hybridization, the filters were removed from the hybridization solution and washed under high stringency conditions (2X SSC, 0.5% SDS, 21° C. for 5 minutes; followed by 2X SSC, 0.1% SDS, 21° C., for 15 minutes; followed by a 2nd 2X SSC, 0.1% SDS, 21 ° C. for 15 minutes; followed by 2X SSC, 0.1% SDS, 65° C. for 10 minutes).

The filters were wrapped in plastic wrap and exposed to X-ray film for overnight to 3 days at −80° C., with the aid of an intensifying screen. The autoradiographs were developed and positively hybridizing transformants of various signal intensities were identified. These positive clones were picked; grown for 5 hours in selective medium and plated at low density (approximately 100 colonies per plate).

Nitrocellulose replicas of the colonies were hybridized to the 32P labelled probe in standard hybridization buffer (6X SSC, 0.5% SDS, 5X Denhardt's, 10 mM EDTA, pH8, 100 mg/ml Bakers Yeast ribonucleic acid) under high stringency conditions (65° C. for 2 hours). After 2 hours hybridization, the filters were removed from the hybridization solution and washed under high stringency conditions (2X SSC, 0.5% SDS, 21° C. for 5 minutes; followed by 2X SSC, 0.1% SDS, 21° C. for 15 minutes; followed by a 2nd 2X SSC, 0.1% SDS 21° C. for 15 minutes; followed by 2X SSC, 0.1% SDS, 65° C. for 10 minutes). The filters were wrapped in plastic wrap and exposed to X-ray film for overnight to 3 days at −80° C., with the aid of an intensifying screen. The autoradiographs were developed and positively hybridizing transformants were identified. Bacterial stocks of purified hybridization positive clones were made and plasmid DNA was isolated. The sequence of the cDNA insert was determined. The cDNA insert contained the sequences of the DNA probe used in the hybridization.

WG67-19 varies from the WG67-SP (sESTsequence) and WG67-16 in that it contains a deletion that removes one codon, i.e., 3 bases (1 amino acid) GCC at bp 47–49 from the WG67-19 full-length sequence. WG67-16 varies from WG67-SP (the sEST sequence) (SEQ ID NO 7) in that it lacks 35 bases (bp 42–76) in the WG67-16 sequence provided; this resulted in deletion of the initiator Met and therefore required repair before expression. WG67-16 and WG67-19 diverge at the 3' end of their sequences at bp 764 of WG67-19 and terminate 28 amino acids after the point of divergence. In a COS expression system, clone WG67-19 produces a secreted protein.

EXAMPLE 2

Cartilage Activity Assays

A. Description of W-20 cells

Use of the W-20 bone marrow stromal cells as an indicator cell line is based upon the conversion of these cells to osteoblast-like cells after treatment with an osteogenic protein, such as a BMP protein (Thies et al, Journal of Bone and Mineral Research, 5:305 (1990); and Thies et al, Endocrinology, 130:1318 (1992)). Specifically, W-20 cells are a clonal bone marrow stromal cell line derived from adult mice by researchers in the laboratory of Dr. D. Nathan, Children's Hospital, Boston, Mass. Treatment of W-20 cells with certain BMP proteins results in (1) increased alkaline phosphatase production, (2) induction of PTH stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date we have observed conversion of W-20 stromal cells to osteoblast-like cells only upon treatment with BMPs. In this manner, the in vitro activities displayed by BMP treated W-20 cells correlate with the in vivo bone forming activity known for BMPs.

Below two in vitro assays useful in comparison of BMP activities of novel osteoinductive molecules are described.

B. W-20 Alkaline Phosphatase Assay Protocol

W-20 cells are plated into 96 well tissue culture plates at a density of 10,000 cells per well in 200 $\mu$l of media (DME with 10% heat inactivated fetal calf serum, 2 mM glutamine and 100 Units/ml penicillin+100 $\mu$g/ml streptomycin. The cells are allowed to attach overnight in a 95% air, 5% $CO_2$ incubator at 37° C. The 200 $\mu$l of media is removed from each well with a multichannel pipettor and replaced with an equal volume of test sample delivered in DME with 10% heat inactivated fetal calf serum, 2 mM glutamine and 1% penicillin-streptomycin. Test substances are assayed in triplicate. The test samples and standards are allowed a 24 hour incubation period with the W-20 indicator cells. After the 24 hours, plates are removed from the 37° C. incubator and the test media are removed from the cells. The W-20 cell layers are washed 3 times with 200 $\mu$l per well of calcium/magnesium free phosphate buffered saline and these washes are discarded. 50 $\mu$l of glass distilled water is added to each well and the assay plates are then placed on a dry ice/ethanol bath for quick freezing. Once frozen, the assay plates are removed from the dry ice/ethanol bath and thawed at 37° C. This step is repeated 2 more times for a total of 3 freeze-thaw procedures. Once complete, the membrane bound alkaline phosphatase is available for measurement. 50 $\mu$l of assay mix (50 mM glycine, 0.05% Triton X-100, 4 mM $MgCl_2$, 5 mM p-nitrophenol phosphate, pH=10.3) is added to each assay well and the assay plates are then incubated for 30 minutes at 37° C. in a shaking waterbath at 60 oscillations per minute. At the end of the 30 minute incubation, the reaction is stopped by adding 100 $\mu$l of 0.2 N NaOH to each well and placing the assay plates on ice. The spectrophotometric absorbance for each well is read at a wavelength of 405 nanometers. These values are then compared to known standards to give an estimate of the alkaline phosphatase activity in each sample. Using known amounts of p-nitrophenol phosphate, absorbance values are generated. Absorbance values for known amounts of BMPs are determined and converted to $\mu$ moles of p-nitrophenol phosphate cleaved per unit time. These values are then used to compare the activities of known amounts of Frazzled protein to BMP-2.

C. Osteocalcin RIA Protocol

W-20 cells are plated at $10^6$ cells per well in 24 well multiwell tissue culture dishes in 2 mls of DME containing 10% heat inactivated fetal calf serum, 2 mM glutamine. The cells are allowed to attach overnight in an atmosphere of 95% air 5% $CO_2$ at 37° C. The next day the medium is changed to DME containing 10% fetal calf serum, 2 mM glutamine and the test substance in a total volume of 2 ml. Each test substance is administered to triplicate wells. The test substances are incubated with the W-20 cells for a total of 96 hours with replacement at 48 hours by the same test medias. At the end of 96 hours, 50 $\mu$l of the test media is removed from each well and assayed for osteocalcin production using a radioimmunoassay for mouse osteocalcin. The details of the assay are described in the kit manufactured by Biomedical Technologies Inc., 378 Page Street, Stoughton, Mass. 02072. Reagents for the assay are found as product numbers BT-431 (mouse osteocalcin standard), BT-432 (Goat anti-mouse Osteocalcin), BT-431R (iodinated mouse osteocalcin), BT-415 (normal goat serum) and BT414 (donkey anti goat IgG). The RIA for osteocalcin synthesized by W-20 cells in response to BMP treatment is carried out as described in the protocol provided by the manufacturer.

The values obtained for the test samples are compared to values for known standards of mouse osteocalcin and to the amount of osteocalcin produced by W-20 cells in response to challenge with known amounts of BMP-2.

D. Rosen Modified Sampath-reddi Assay

A modified version of the rat bone formation assay described in Sampath and Reddi, Proc. Natl. Acad. Sci. USA, 80:6591–6595 (1983) is used to evaluate bone and/or cartilage and/or other connective tissue activity of novel osteoinductive or chondroinductive proteins. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then equilibrated to 0.1% TFA. The resulting solution is added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 7–14 days. Half of each implant is used for alkaline phosphatase analysis (see, Reddi et al, Proc. Natl. Acad. Sci., 69:1601 (1972)).

The other half of each implant is fixed and processed for histological analysis. 1 $\mu$m glycolmethacrylate sections are stained with Von Kossa and acid fuschin to score the amount of induced bone and cartilage and other connective tissue formation present in each implant. The terms +1 through +5 represent the area of each histological section of an implant occupied by new bone and/or cartilage cells and matrix. A score of +5 indicates that greater than 50% of the implant is new bone and/or cartilage produced as a direct result of protein in the implant. A score of +4, +3, +2, and +1 indicates that greater than 40%, 30%, 20% and 10% respectively of the implant contains new cartilage and/or bone.

Alternatively, the implants are inspected for the appearance of tissue resembling embryonic tendon, which is easily recognized by the presence of dense bundles of fibroblasts oriented in the same plane and packed tightly together. (Tendon/ligament-like tissue is described, for example, in Ham and Cormack, Histology (J B Lippincott Co. (1979)), pp. 367–369, the disclosure of which is hereby incorporated by reference]. These findings are reproduced in additional assays in which tendon/ligament-like tissues are observed in the Frazzled protein containing implants. The Frazzled proteins are assessed for activity in this assay.

Using Northern analysis, proteins can be tested for their effects on various cell lines. Suitable cell lines include cell lines derived from E13 mouse limb buds. After 10 days of treatment with protein, the cell phenotype is examined histologically for indications of tissue differentiation. In addition, Northern analysis of mRNA from protein treated cells can be performed for various markers including one or more of the following markers for bone, cartilage and/or tendon/ligament as follows:

| Marker | Bone | Cartilage | Tendon/Ligament |
|---|---|---|---|
| Osteocalcin | + | − | − |
| Alkaline Phosphatase | + | − | − |
| Proteoglycan Core Protein | +/−[1] | + | +[2] |
| Collagen Type I | + | + | + |
| Collagen Type II | +/−[1] | + | +[2] |
| Decorin | + | + | + |
| Elastin | +/−[3] | ? | + |

[1]- Marker seen early, marker not seen as mature bone tissue forms
[2]- Marker depends upon site of tendon; strongest at bone interface
[3]- Marker seen at low levels

EXAMPLE 3

Full Thickness Articular Cartilage Repair Model

A full thickness articular cartilage defect model in the femoral-patellar joint of adult rabbits is used to evaluate the ability of the Frazzled proteins to affect cartilage and bone repair. Adult New Zealand White rabbits are anesthetized and prepared for sterile surgery. A 3×3 mm defect through the articular cartilage and into underlying subchondral bone is drilled into the patellar groove of the knee joint. The defect is either left empty, filled with collagen sponge (controls), or with collagen sponge soaked with an effective amount, e.g., 10 μg of the test (experimental) Frazzled proteins. The incision is closed and animals are allowed free movement within their cages for 4 weeks. After 4 weeks the animals are humanely euthanatized and the articular cartilage/subchondral bone defect is evaluated histologically for tissue architecture, quantity, and quality of repair tissue.

After 4 weeks, the repair tissue which contains a test Frazzled proteins is examined for signs of accelerated healing of the subchondral bone as compared to the controls. The newly formed repair cartilage above the subchondral bone contains cells which show architectural characteristics and staining properties similar to normal hyaline articular cartilage. The Frazzled proteins are examined for activity which augments the ability of tissue within an osteochondral defect to regenerate cartilage having characteristics more consistent with normal hyaline articular cartilage.

EXAMPLE 4

Embryonic Development Assay

Activities are assayed using tissue derived from gastrula stage *Xenopus laevis* embryos in which many inductive interactions are ongoing. These include induction of the neuroectoderm and the mesoderm, notably muscle and blood progenitors. The activity of novel genes can be assayed by ectopically expressing them in the embryo (as micro- injected mRNAs) and analysing the consequences. The Frazzled proteins of the invention were analyzed for activity.

A. in situ hybridization

Albino embryos are collected at various stages for fixation, permeabilized with proteinase K and pre-hybridized. They are then hybridized over night with digoxygenin-labeled riboprobes. Embryos are washed, treated with RNase A and T1 to remove background and blocked with Boehringer Mannheim Blocking Reagent. Embryos are incubated with alkaline phosphatase-conjugated anti-digoxygenin antibody for four hours at room temperature, washed extensively before chromogenic reaction with alkaline phosphatase substrate. Embryos are then re-fixed and de-stained to remove background for photography.

B. Gain-of-function phenotype in whole embryos

Embryos injected with synthetic RNA encoding WG67 or DNA constructs expressing this gene fail to elongate. Muscle formation is disrupted and a large increase in gut volume is noted by hatching stages. This increase may be due to an increase in the length of intestine, since an increase in gut loops can be seen.

Embryos injected with WA628 show attenuated head formation. Some expansion of the gut is seen, but this is much less dramatic than observed with WG67. This difference between WG67 and WA628 in activity profile can be appropriately used to specifically direct the change in tissue type desired to be effectuated.

C. Effects of ectopic expression of WG67 and WA628

Embryos were injected at the two cell stage with synthetic RNA prepared from WA628 or WG67, and were harvested for analysis when control embryos reached tailbud (24 hours after fertilization). WA628 causes embryos to lose anterior neural structures such as forebrain and eyes, with an expansion of the hindbrain and a disruption of neural crest migration. WG67 apparently causes embryos to lose ventral tissue with an over representation of dorsal structures such as the forebrain and cement gland (chin primordium). These phenotypes can be caused by antagonizing wnt protein-mediate signal transduction pathways.

D. Whole embryo assay

Embryos are micro-injected with 50 pg or 100 pg in vitro synthesized, capped RNA at 2-cell or 4-cell stages. β-galactosidase RNA is included as lineage tracer to determine the extent of diffusion of the injected RNA. The product of the β-gal RNA is visualized histochemically, by X-gal staining. The target area of these micro-injections are dorsal marginal zone or ventral marginal zone of one of the 2 or 4 cells. Embryos are left to develop until desired stages before harvested for fixation, X-gal staining and photography.

E. Expression profile

WG67 expression is zygotic. It is always ventrally restricted to a quadrant 60° to 90° centered on the ventral midline. At early gastrula, WG67 expression is restricted to the posterior ectoderm and mesoderm. By early neurula, expression becomes more anterior, where it overlies the heart primordium. WG 67 is also expressed in the mesoderm of the future blood forming region and in the overlying ectoderm.

WA628 expression is predominantly zygotic, with expression by late neurula in the forebrain region.

F. Animal cap assay

Embryos are micro-injected with 50 to 400 pg capped RNA in animal pole of one cell at 2-cell stage. Globin RNA is used as a control. Embryos are left to develop until stage 8. Cells at the animal pole of embryos are micro-dissected (animal caps) and cultured until sibling intact, uninjected embryos reaching stages 14 or 19. 15 animal caps micro-injected with the same RNA (experimental or globin) are pooled for total RNA preparation. Five intact embryos are used for preparation of whole embryo control RNA. These RNA samples are reverse transcribed using random hexamer as primers for cDNA. These DNA samples are subjected to PCR using gene-specific primer pairs at the presence of 32P-dCTP to assay for the presence of corresponding mRNAs in the original RNA samples. The primer pairs used and cycle number for each pair are optimized. The products of these PCR reactions are subsequently resolved on polyacrylamide gels.

Changes in the types of tissues formed are observed and indicate a role of the Frazzleds of the invention in haematopoiesis, brain formation, gut formation, and concomitant muscle tissue suppression.

EXAMPLE 5

Cloning of Frazzled Homologues

Other species, in particular human, have DNA sequences homologous to Xenopus Frazzleds. DNA sequences encoding for example, human Frazzleds are isolated by various techniques known to those skilled in the art. The invention, therefore, includes DNA sequences encoding human Frazzleds and methods for obtaining them. Such methods utilize the Xenopus Frazzled nucleotide sequences or portions in the design of probes to screen libraries for the human gene or coding sequences or fragments thereof using standard techniques.

According to the methods, a Xenopus sequence or a portion thereof is used as a probe to screen a human genomic library under reduced stringency conditions (e.g., 0.2X SSC, 0.1% SDS, 50° C.) or as a probe to identify a human cell line or tissue which synthesizes the analogous human Frazzled protein. A human genomic library, such as Stratagene catalog #945200 or Clonetech catalog #HL1067j, can be screened with such a probe, and positives isolated and their DNA sequence determined.

A human coding sequence is used as a probe to identify a human cell line or tissue which synthesizes Frazzled mRNA. Alternatively, the Xenopus coding sequence is used as a probe to identify such human cell line or tissue. Briefly described, RNA is extracted from a selected cell or tissue source and either electrophoresed on a formaldehyde agarose gel and transferred to nitrocellulose, or reacted with formaldehyde and spotted on nitrocellulose directly. The nitrocellulose is then hybridized under reduced stringency conditions to a probe derived from a coding sequence of the Xenopus or human Frazzled. Human cell lines and tissues which are a particularly suitable source of Frazzled mRNA include for example, muscle, skeletal muscle, cardiac muscle, placenta, brain and neuronal tissues. Additional sources include lung, pancreas, liver, spleen, kidney, testes, intestines as well as other cell line and tissues.

Alternatively, the Xenopus frazzled coding sequence is used to design oligonucleotide primers which will specifically amplify a portion of the Frazzled encoding sequence located in the region located between the primers utilized to perform the specific amplification reaction. Utilizing Xenopus and human frazzled sequences one can specifically amplify corresponding human Frazzled encoding sequences from mRNA, cDNA or genomic DNA templates. Once a positive source has been identified by one of the above described methods, mRNA is selected by oligo (dT) cellulose chromatography and cDNA is synthesized and cloned in λgt10 or other bacteriophage vectors known to those skilled in the art, for example, ZAP by established techniques.

It is also possible to perform the oligonucleotide primer directed amplification reaction, described above, directly on a pre-established human cDNA or genomic library which has been cloned into a bacteriophage vector. In such cases, a library which yields a specifically amplified DNA product encoding a portion of human Frazzled protein is screened directly, utilizing the fragment of amplified Frazzled encoding DNA as a probe.

Regions containing amino acid sequences which are highly conserved within the Frazzled family of proteins are identified and consensus amino acid sequences of these highly conserved regions are constructed based on the similarity of the corresponding regions of individual Frazzled proteins. Oligonucleotide primers designed on the basis of the amino acid sequence of such conserved sequences allow the specific amplification of the human Frazzled encoding sequences. Two such consensus amino acid sequences are set forth below, the first being less restrictive: consensus amino acid sequence (1):

SEQ ID NO 13: Phe-Leu-Cys-Ala/Ser-Met/Leu-Tyr/Phe-Ala-Pro-Ile/Val-Cys and consensus amino acid sequence (2):

SEQ ID NO 14: Trp-Pro-Glu-Ser/Ile-Leu-Asp/Lys where X/Y indicates that either amino acid residue may appear at that position.

Four additional concensus amino acid sequences include SEQ ID NO 15–18 as follows. For example, to distinguish WA628 homologs, a degenerate 17mer is designed to amino acids 150 to 155 as follows:

SEQ ID NO 15: Thr-Ile-Thr-Asn-Asp-Thr

For example, to distinguish WG67 homologs, a degenerate 17mer is designed to amino acids 141 to 146 as follows:

SEQ ID NO 16: Lys-Glu-Tyr-Gln-Tyr-Ala or, a degenerate 27mer designed to amino acids 141 to 149 as follows:

SEQ ID NO 17: Lys-Glu-Tyr-Gln-Tyr-Ala-Tyr-Lys-Glu

As yet another example, to distinguish both WA628 and WG67 homologs, a 17mer composite probe to cover all possibilities for amino acids 288 to 293 of WA628 and amino acids 275 to 280 of WG67-19 is designed as follows:

SEQ ID NO 18: Trp-Lys/Arg-Asn/His-His-Lys-Cys

Degenerate oligonucleotide primers that encode amino acid sequences of SEQ ID NO 13, 14, 15, 16, 17, and/or 18, are synthesized on an automated DNA synthesizer. These oligonucleotides are utilized as primers to allow the specific amplification of a specific nucleotide sequence from human genomic DNA or human cDNA using standard PCR amplification techniques known to those skilled in the art. The products of the amplification reactions result in the identification of human Frazzled encoding sequences. Using standard molecular techniques, these amplification products are used to screen cDNA libraries to obtain clones that contain the complete human Frazzled coding sequences.

Additional methods known to those skilled in the art can also be used to isolate human and other species' Frazzled proteins of the invention.

EXAMPLE 6

Embryonic Stem Cell Assay

The effects of Frazzled proteins of the present invention, on the growth and differentiation effects in vitro on a number of available embryonic stem cell lines can be readily assayed. One such cell line is ES-E14TG2, which is available from the American Type Culture Collection in Rockville, Md.

To conduct the assay, cells are propagated in the presence of 100 units of LIF to maintain them in an undifferentiated state. Assays are setup by first removing the LIF and aggregating the cells in suspension, in what is known as embryoid bodies. After 3 days the embryoid bodies are plated on gelatin coated plates (12 well plates for PCR analysis, 24 well plates for immunocytochemistry) and treated with the proteins to be assayed. Cells are supplied with nutrients and treated with the protein factor every 2–3 days. Cells may be adapted so that assays may be conducted in media supplemented with 15% Fetal Bovine Serum (FBS) or with CDM defined media containing much lower amounts of FBS.

At the end of the treatment period (ranging from 7–21 days) RNA is harvested from the cells and analyzed by quantitative multiplex PCR for the following markers: Brachyury, a mesodermal marker, AP-2, an ectodermal marker, and HNF-3 an endodermal marker. Through immunocytochemistry, it is also possible to detect the differentiation of neuronal cells (glia and neurons), muscle cells (cardiomyocytes, skeletal and smooth muscle), and various other phenotype markers such as proteoglycan core protein (cartilage), and cytokeratins (epidermis). As these cells have a tendency to differentiate autonomously when LIF is removed, the results are always quantitated by comparison to an untreated control.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

All cited publications and patent documents are hereby incorporated by reference for their disclosure cited herein.

What is claimed is:

1. An isolated DNA molecule comprising a DNA sequence selected from the group consisting of:
   (a) nucleotides #44 to #889 of SEQ ID NO: 1;
   (b) nucleotides #8 to #850 of SEQ ID NO:3;
   (c) nucleotides #80 to #967 of SEQ ID NO:5;
   (d) SEQ ID NO:7;
   (e) nucleotides #89 to #889, #92 to #889, #95 to #889, or #98 to #889 of SEQ ID NO:1;
   (f) nucleotides #53 to #850, #56 to #850, #59 to #850, or #62 to #850 of SEQ ID NO:3;
   (g) nucleotides #152 to #967, #155 to #967, or #158 to #967 of SEQ ID NO:5;
   (h) nucleotides encoding a fragment of the amino acid sequence of SEQ ID NO:2, the fragment comprising SEQ ID NO:17;
   (I) nucleotides encoding a fragment of the amino acid sequence of SEQ ID NO:4, the fragment comprising SEQ ID NO:17; and
   (j) nucleotides encoding a fragment of the amino acid sequence of SEQ ID NO:6, the fragment comprising SEQ ID NO: 13.

2. A vector comprising a DNA molecule of claim 1 in operative association with an expression control sequence therefor.

3. A host cell transformed with a vector of claim 2.

4. The isolated DNA molecule of claim 1 comprising nucleotides #89 to #889, #92 to #889, #95 to #889, or #98 to #889 of SEQ ID NO:1.

5. The isolated DNA molecule of claim 1 comprising nucleotides #53 to #850, #56 to #850, #59 to #850, or #62 to #850 of SEQ ID NO:3.

6. The isolated DNA molecule of claim 1 comprising nucleotides #152 to #967, #155 to #967, or #158 to #967 of SEQ ID NO:5.

7. An isolated DNA molecule that hybridizes to a DNA molecule consisting of a sequence selected from the group consisting of:
(a) nucleotides #44 to #889 of SEO ID NO:1;
(b) nucleotides #8 to #850 of SEO ID NO:3;
(c) nucleotides #80 to #967 of SEQ ID NO:5:
(d) SEO ID NO:7;
(e) nucleotides #89 to #889, #92 to #889, #95 to #889, or #98 to #889 of SEQ ID NO:1;
(f) nucleotides #53 to #850, #56 to #850, 59 to #850, or #62 to #850 of SEQ ID NO:3;
(g) nucleotides #152 to #967. #155 to #967, or #158 to #967 of SEQ ID NO:5;
(h) SEQ ID No 1: and
(i) SEQ ID No:3
when incubated in 6XSSC at 65° C. for at least two hours, then washed in 2XSSC and 0.1% SDS at 65° C. for 10 minutes.

8. An isolated DNA molecule comprising a DNA sequence selected from the group consisting of:
(a) nucleotides encoding the amino acids of SEQ ID NO:2;
(b) nucletotides encoding the amino acids of SEQ ID NO:4; and
(c) nucleotides encoding the amino acids of SEQ ID NO:6.

9. A vector comprising a DNA molecule of claim 8 in operative association with an expression control sequence therefor.

10. A host cell transformed with a vector of claim 9.

11. A method for producing a protein encoded by the DNA molecule of claim 8, said method comprising the steps of:
(a) culturing a host cell transformed with a DNA molecule according to claim 8;
(b) expressing said protein; and
(c) recovering said protein.

12. An isolated DNA molecule comprising a DNA sequence selected from the group consisting of:
(a) nucleotides #44 to #889 of SEQ ID NO:1;
(b) nucleotides #8 to #850 of SEQ ID NO:3;
(c) nucleotides #80 to #967 of SEQ ID NO:5; and
(d) SEQ ID NO:7.

13. A vector comprising a DNA molecule of claim 12 in operative association with an expression control sequence therefor.

14. A host cell transformed with the vector of claim 13.

15. An isolated DNA molecule comprising nucleotides #44 to #889 of SEQ ID NO:1.

16. An isolated DNA molecule comprising nucleotides #8 to #850 of SEQ ID NO:3.

17. An isolated DNA molecule comprising nucleotides #80 to #867 of SEQ ID NO:5.

18. An isolated DNA molecule comprising SEQ ID NO:7.

19. An isolated DNA molecule comprising a DNA sequence selected from the group consisting of:
(a) the DNA sequence of the WA628 clone deposited under accession number ATCC 984301;
(b) the DNA sequence of the full-length protein coding sequence of the WA628 clone deposited under accession number ATCC 98430;
(c) nucleotides encoding the full-length protein encoded by the WA628 clone deposited under accession number ATCC 98430;
(d) the DNA sequence of a mature protein coding sequence of the WA628 clone deposited under accession number ATCC 98430: and
(e) nucleotides encoding a mature protein encoded by the WA628 clone deposited under accession number ATCC 98430.

20. The isolated DNA molecule of claim 19 comprising the DNA sequence of the WA628 clone deposited under accession number ATCC 98430.

21. The isolated DNA molecule of claim 19 comprising the DNA sequence of the full-length protein coding sequence of the WA628 clone deposited under accession number ATCC 98430.

22. The isolated DNA molecule of claim 19 comprising nucleotides encoding the full-length protein encoded by the WA628 clone deposited under accession number ATCC 98430.

23. The isolated DNA molecule of claim 19 comprising the DNA sequence of a mature protein coding sequence of the WA628 clone deposited under accession number ATCC 98430.

24. The isolated DNA molecule of claim 19 comprising nucleotides encoding a mature protein encoded by the WA628 clone deposited under accession number ATCC 98430.

25. An isolated DNA molecule comprising a DNA sequence selected from the group consisting of:
(a) the DNA sequence of the WG67-16 clone deposited under accession number ATCC 98432;
(b) the DNA sequence of the full-length protein coding sequence of the WG67-16 clone deposited under accession number ATCC 98432;
(c) nucleotides encoding the full-length protein encoded by the WG67-16 clone deposited under accession number ATCC 98432;
(d) the DNA sequence of a mature protein coding sequence of the WG67-16 clone deposited under accession number ATCC 98432; and
(e) nucleotides encoding a mature protein encoded by the WG67-16 clone deposited under accession number ATCC 98432.

26. The isolated DNA molecule of claim 25 comprising the DNA sequence of the WG67-16 clone deposited under accession number ATCC 98432.

27. The isolated DNA molecule of claim 25 comprising the DNA sequence of the full-length protein coding sequence of the WG67-16 clone deposited under accession number ATCC 98432.

28. The isolated DNA molecule of claim 25 comprising nucleotides encoding the full-length protein encoded by the WG67-16 clone deposited under accession number ATCC 98432.

29. The isolated DNA molecule of claim 25 comprising the DNA sequence of a mature protein coding sequence of the WG67-16 clone deposited under accession number ATCC 98432.

30. The isolated DNA molecule of claim 25 comprising nucleotides encoding a mature protein encoded by the WG67-16 clone deposited under accession number ATCC 98432.

31. An isolated DNA molecule comprising a DNA sequence selected from the group consisting of:
   (a) the DNA sequence of the WG67-19 clone deposited under accession number ATCC 98434;
   (b) the DNA sequence of the full-length protein coding sequence of the WG67-19 clone deposited under accession number ATCC 98434;
   (c) nucleotides encoding the full-length protein encoded by the WG67-19 clone deposited under accession number ATCC 98434;
   (d) the DNA sequence of a mature protein coding sequence of the WG67-19 clone deposited under accession number ATCC 98434; and
   (e) nucleotides encoding a mature protein encoded by the WG67-19 clone deposited under accession number ATCC 98434.

32. The isolated DNA molecule of claim 31 comprising the DNA sequence of the WG67-19 clone deposited under accession number ATCC 98434.

33. The isolated DNA molecule of claim 31 comprising the DNA sequence of the full-length protein coding sequence of the WG67-19 clone deposited under accession number ATCC 98434.

34. The isolated DNA molecule of claim 31 comprising nucleotides encoding the full-length protein encoded by the WG67-19 clone deposited under accession number ATCC 98434.

35. The isolated DNA molecule of claim 31 comprising the DNA sequence of a mature protein coding sequence of the WG67-19 clone deposited under accession number ATCC 98434.

36. The isolated DNA molecule of claim 31 comprising nucleotides encoding a mature protein encoded by the WG67-19 clone deposited under accession number ATCC 98434.

37. A method of producing a protein encoded by SEQ ID NO:1, said method comprising the steps of:
   (a) culturing a host cell transformed with a DNA molecule comprising
      SEQ ID NO:1;
   (b) expressing said protein; and
   (c) recovering said protein.

38. A method of producing a protein encoded by SEQ ID NO:3, said method comprising the steps of:
   (a) culturing a host cell transformed with a DNA molecule comprising SEQ ID NO:3;
   (b) expressing said protein: and
   (c) recovering said protein.

39. A method of producing a protein encoded by SEQ ID NO:5, said method comprising the steps of:
   (a) culturing a host cell transformed with a DNA molecule comprising
      SEQ ID NO:5;
   (b) expressing said protein; and
   (c) recovering said protein.

* * * * *

```
                            SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
        (A) LENGTH: 2190 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 44..889

(xi) SEQUENCE DESCRIPTION: SEQ ID NO:1:

GAATTCCATA GCAACAAACA GTACCCATAG CAACAAACAG TAC ATG ACT GGA GTC          55
                                              Met Thr Gly Val
                                                1

TTC CTG CTC CTC TGC GCC TCC ATG CTG GCC GCC GCC GCC GCC TTT GAC        103
Phe Leu Leu Leu Cys Ala Ser Met Leu Ala Ala Ala Ala Ala Phe Asp
  5                  10                  15                  20

ATT GGA TTA TCC ACC AAG TGC GTT CCC ATT CCC AAA GAG ATG GCC ATG        151
Ile Gly Leu Ser Thr Lys Cys Val Pro Ile Pro Lys Glu Met Ala Met
                 25                  30                  35

TGC AAT GAC GTC GGC TAC TCG GAG ATG CGG TTG CCA AAC CTG TTG GGA        199
Cys Asn Asp Val Gly Tyr Ser Glu Met Arg Leu Pro Asn Leu Leu Gly
             40                  45                  50

CAC ACT AAC ATG GCA GAA GTC GTG CCC AAG TCA GCA GAG TGG CAG AAC        247
His Thr Asn Met Ala Glu Val Val Pro Lys Ser Ala Glu Trp Gln Asn
         55                  60                  65

CTC CTA CAG ACC GGC TGC CAC CCC TAT GCC AGG ACC TTC CTA TGC TCC        295
Leu Leu Gln Thr Gly Cys His Pro Tyr Ala Arg Thr Phe Leu Cys Ser
     70                  75                  80

CTA TTC GCC CCA GTC TGC CTG GAC ACG TTC ATC CAG CCC TGC CGC AGC        343
Leu Phe Ala Pro Val Cys Leu Asp Thr Phe Ile Gln Pro Cys Arg Ser
 85                  90                  95                 100
```

```
ATG TGT GTT GCT GTA AGA AAC AGT TGT GCT CCA GTT CTG GCA TGT CAT       391
Met Cys Val Ala Val Arg Asn Ser Cys Ala Pro Val Leu Ala Cys His
            105                 110                 115

GGG CAC TCC TGG CCT GAG AGC TTA GAC TGT GAC AGG TTC CCA GCT GGG       439
Gly His Ser Trp Pro Glu Ser Leu Asp Cys Asp Arg Phe Pro Ala Gly
            120                 125                 130

GAA GAC ATG TGT CTG GAC ACT CTC AGC AAA GAG TAT CAG TAT GCC TAT       487
Glu Asp Met Cys Leu Asp Thr Leu Ser Lys Glu Tyr Gln Tyr Ala Tyr
            135                 140                 145

AAA GAA CTG CCA AAG CCA AGC TGC CAG GGC TGC CCA CTT ATT GAA GAA       535
Lys Glu Leu Pro Lys Pro Ser Cys Gln Gly Cys Pro Leu Ile Glu Glu
    150                 155                 160

TTC TTT TCA CAC AAG ACA GTC TTG GAA GCT TTT TGT GAC AAT AAC TTT       583
Phe Phe Ser His Lys Thr Val Leu Glu Ala Phe Cys Asp Asn Asn Phe
165                 170                 175                 180

GCT GTT AAA GTG AAA TTG GCA AAG AAG AAA ACA ACT TCA GGA CTT CAT       631
Ala Val Lys Val Lys Leu Ala Lys Lys Lys Thr Thr Ser Gly Leu His
                185                 190                 195

GAA TAT GAG ACC GAA GGC CCA GTT GAG TTC ATT AAA CAA GGT CTG CTC       679
Glu Tyr Glu Thr Glu Gly Pro Val Glu Phe Ile Lys Gln Gly Leu Leu
            200                 205                 210

CTT CCA TAT GAC ACA CGT ACC ATG ATT GAA CAG TGG CTG CTG ATT AAT       727
Leu Pro Tyr Asp Thr Arg Thr Met Ile Glu Gln Trp Leu Leu Ile Asn
            215                 220                 225

GAG AAT TGT GCT CAG AAG CTG ATA CGG AAC AGA CCC ACA GTG TAT GTT       775
Glu Asn Cys Ala Gln Lys Leu Ile Arg Asn Arg Pro Thr Val Tyr Val
            230                 235                 240

ATT GCT GGT GAC ATC CAT CAT GGA AAG ATT AAA ATC TTC TGC TCC CCC       823
Ile Ala Gly Asp Ile His His Gly Lys Ile Lys Ile Phe Cys Ser Pro
245                 250                 255                 260

TGT GTA CTC AGA GAA TGG AAC ACG ACT TAC TTT TTC AGG CAG AGA CTA       871
Cys Val Leu Arg Glu Trp Asn Thr Thr Tyr Phe Phe Arg Gln Arg Leu
            265                 270                 275

TAC ATT ACA AGA ATT TGA AAATAACAAA AAAATTCACC AGCACCTCGG              919
Tyr Ile Thr Arg Ile *
            280

ACTACCAAAT GAGCGTCTTG CTCTATATGT CCTTAGAAAT CAAGGGCTTG TTCCGGAGCA      979

TGTTGAAACT AGAACTTTGT ATAGCACTTT CCAGCCAAAC ATTTCCCAGG GGAAACTAGA     1039

AATGTGGGTT GATGTTTTTC CAAAAAGTTT AGGACCTCCT GGACCACCAT TCAATATTAC     1099

TCCTCGCAAA GCAAAGAAGT ATGTACTTCG TGTTATCGTT TGGAATACCA AAGATGTCAT     1159

TCTAGATGAG AAAAGTATTA CTGGAGAAGA AATGAGTGAT ATTTATGTGA AGGGGTGGAT     1219

TCCTGGCAAT GAAGAAAATA AGCAGAAAAC AGATGTGCAC TACAGGTCAC TGGATGGGGA     1279

AGGAAACTTT AACTGGAGAT TGTTTTTTCC ATTTGAATAT CTGCCGGCCG AACAGCTGTG     1339

CATTGTTTCT AAAAAGGAAC ATTTCTGGAG CCTTGACAAT ACAGAATTTA AGCTGCCACC     1399

CAAACTAATT CTTCAGATAT GGGACAATGA TAAATTCTCC TTGGATGACT ATTTAGGTTT     1459

TGTAGAACTT GATTTACATC GAGCAACAAT GCCTGCAAAA GTTCCAGAGA ATGCACTTTT     1519

AGACTTAGTT GACCAGGCCA ACCATTCAAA GGTGGCCTCT CTGTTTGAGC AGAAATCCAT     1579

GAAGGGATGG TGGCCATGCT ATGCAGAAAA AGATGGAAAA CGGATATTAT CTGGGAAAAT     1639

TGAGATGACC CTTGAGGTAC TGAATGAAAA AGAGGCTGAC GAACGGCCTG CTGGCAAGGG     1699

ACGAGATGAG CCCAACATGA ACCCCAAGTT AGAGCTACCA AACCGGCCAG ACACCTCCTT     1759

CCTCTGGTTT ACAAACCCAT GCAAGACCAT GAAATTTATC ATATGGCGCA GATTTAAATG     1819

GGTATTTATT GGACTCATCG TCCTGCTCCT TGTACTTCTG TTCCTTGCAG TCTTCTTCTA     1879
```

```
TTCTTTGCCG GGCTATGTTT CTATGAAGAT TGTGAAACCC AATGTATAAG AACAGCAACG    1939

AAATGCCAAC ATGGACCATA CTCTCCCTAC TTAACTTAAT GAATTTATAT TCTTAAAACT    1999

TGAAAAAAGA GACAAAGTGA ATCTTAGAGA AAAAAAACAC CCACCACGTA CTTTATTTCA    2059

CACAAGCCTT GGGTGCAGGG TTCAACATTT GTACACTTAT ATACAAAGCT TACATATCAC    2119

TACTTTTTTT ATTCCATGGG TTCACACTCA ACTGTGATAA TGTGTTTTTC TCTTTATAAT    2179

AGAACCATAT G                                                         2190
```

(2) INFORMATION FOR SEQ ID NO:2:

(i) SEQUENCE CHARACTERISTICS:
        (A) LENGTH: 281 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Gly Val Phe Leu Leu Cys Ala Ser Met Leu Ala Ala Ala
 1               5                  10                  15

Ala Ala Phe Asp Ile Gly Leu Ser Thr Lys Cys Val Pro Ile Pro Lys
             20                  25                  30

Glu Met Ala Met Cys Asn Asp Val Gly Tyr Ser Glu Met Arg Leu Pro
         35                  40                  45

Asn Leu Leu Gly His Thr Asn Met Ala Glu Val Val Pro Lys Ser Ala
     50                  55                  60

Glu Trp Gln Asn Leu Leu Gln Thr Gly Cys His Pro Tyr Ala Arg Thr
 65                  70                  75                  80

Phe Leu Cys Ser Leu Phe Ala Pro Val Cys Leu Asp Thr Phe Ile Gln
                 85                  90                  95

Pro Cys Arg Ser Met Cys Val Ala Val Arg Asn Ser Cys Ala Pro Val
            100                 105                 110

Leu Ala Cys His Gly His Ser Trp Pro Glu Ser Leu Asp Cys Asp Arg
        115                 120                 125

Phe Pro Ala Gly Glu Asp Met Cys Leu Asp Thr Leu Ser Lys Glu Tyr
    130                 135                 140

Gln Tyr Ala Tyr Lys Glu Leu Pro Lys Pro Ser Cys Gln Gly Cys Pro
145                 150                 155                 160

Leu Ile Glu Glu Phe Phe Ser His Lys Thr Val Leu Glu Ala Phe Cys
                165                 170                 175

Asp Asn Asn Phe Ala Val Lys Val Lys Leu Ala Lys Lys Lys Thr Thr
            180                 185                 190

Ser Gly Leu His Glu Tyr Glu Thr Glu Gly Pro Val Glu Phe Ile Lys
        195                 200                 205

Gln Gly Leu Leu Leu Pro Tyr Asp Thr Arg Thr Met Ile Glu Gln Trp
    210                 215                 220

Leu Leu Ile Asn Glu Asn Cys Ala Gln Lys Leu Ile Arg Asn Arg Pro
225                 230                 235                 240

Thr Val Tyr Val Ile Ala Gly Asp Ile His His Gly Lys Ile Lys Ile
                245                 250                 255

Phe Cys Ser Pro Cys Val Leu Arg Glu Trp Asn Thr Thr Tyr Phe Phe
            260                 265                 270

Arg Gln Arg Leu Tyr Ile Thr Arg Ile
        275                 280
```

(2) INFORMATION FOR SEQ ID NO:3:

(i) SEQUENCE CHARACTERISTICS:
        (A) LENGTH: 1140 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 8..850

(xi) SEQUENCE DESCRIPTION: SEQ ID NO:3:

```
CTCGAGC ATG ACT GGA GTC TTC CTG CTC CTC TGC GCC TCC ATG CTG GCC         49
        Met Thr Gly Val Phe Leu Leu Leu Cys Ala Ser Met Leu Ala
        1               5                   10

GCC GCC GCC TTT GAC ATT GGA TTA TCC ACC AAG TGC GTT CCC ATT CCC         97
Ala Ala Ala Phe Asp Ile Gly Leu Ser Thr Lys Cys Val Pro Ile Pro
15              20                  25                  30

AAA GAG ATG GCC ATG TGC AAT GAC GTC GGC TAC TCG GAG ATG CGG TTG         145
Lys Glu Met Ala Met Cys Asn Asp Val Gly Tyr Ser Glu Met Arg Leu
            35                  40                  45

CCA AAC CTG TTG GGA CAC ACT AAC ATG GCA GAA GTC GTG CCC AAG TCA         193
Pro Asn Leu Leu Gly His Thr Asn Met Ala Glu Val Val Pro Lys Ser
        50                  55                  60

GCA GAG TGG CAG AAC CTC CTA CAG ACC GGC TGC CAC CCC TAT GCC AGG         241
Ala Glu Trp Gln Asn Leu Leu Gln Thr Gly Cys His Pro Tyr Ala Arg
        65                  70                  75

ACC TTC CTA TGC TCC CTA TTC GCC CCA GTC TGC CTG GAC ACG TTC ATC         289
Thr Phe Leu Cys Ser Leu Phe Ala Pro Val Cys Leu Asp Thr Phe Ile
80                  85                  90

CAG CCC TGC CGC AGC ATG TGT GTT GCT GTA AGA AAC AGT TGT GCT CCA         337
Gln Pro Cys Arg Ser Met Cys Val Ala Val Arg Asn Ser Cys Ala Pro
95                  100                 105                 110

GTT CTG GCA TGT CAT GGG CAC TCC TGG CCT GAG AGC TTA GAC TGT GAC         385
Val Leu Ala Cys His Gly His Ser Trp Pro Glu Ser Leu Asp Cys Asp
                115                 120                 125

AGG TTC CCA GCT GGG GAA GAC ATG TGT CTG GAC ACT CTC AGC AAA GAG         433
Arg Phe Pro Ala Gly Glu Asp Met Cys Leu Asp Thr Leu Ser Lys Glu
            130                 135                 140

TAT CAG TAT GCC TAT AAA GAA CTG CCA AAG CCA AGC TGC CAG GGC TGC         481
Tyr Gln Tyr Ala Tyr Lys Glu Leu Pro Lys Pro Ser Cys Gln Gly Cys
        145                 150                 155

CCA CTT ATT GAA GAA TTC TTT TCA CAC AAG ACA GTC TTG GAA GCT TTT         529
Pro Leu Ile Glu Glu Phe Phe Ser His Lys Thr Val Leu Glu Ala Phe
160                 165                 170

TGT GAC AAT AAC TTT GCT GTT AAA GTG AAA TTG GCA AAG AAG AAA ACA         577
Cys Asp Asn Asn Phe Ala Val Lys Val Lys Leu Ala Lys Lys Lys Thr
175                 180                 185                 190

ACT TCA GGA CTT CAT GAA TAT GAG ACC GAA GGC CCA GTT GAG TTC ATT         625
Thr Ser Gly Leu His Glu Tyr Glu Thr Glu Gly Pro Val Glu Phe Ile
                195                 200                 205

AAA CAA GGT CTG CTC CTT CCA TAT GAC ACA CGT ACC ATG ATT GAA CAG         673
Lys Gln Gly Leu Leu Leu Pro Tyr Asp Thr Arg Thr Met Ile Glu Gln
            210                 215                 220

TGG CTG CTG ATT AAT GAG AAT TGT GCT CAG AAG CTG ATA CGG AAC AGA         721
Trp Leu Leu Ile Asn Glu Asn Cys Ala Gln Lys Leu Ile Arg Asn Arg
        225                 230                 235

CCC ACA GTG TAT GTT ATT GCT GGT GAC ATC CAT CAT GGA AAG GTT AAA         769
Pro Thr Val Tyr Val Ile Ala Gly Asp Ile His His Gly Lys Val Lys
```

```
            240                 245                 250
GTC AAC AGG GTT TTC CAC TGG CAG AAA AAG GAC TCT CAG CTG ACA CTT        817
Val Asn Arg Val Phe His Trp Gln Lys Lys Asp Ser Gln Leu Thr Leu
255                 260                 265                 270

GCC ACA AGG AGG TGG AGA CAC CAT AAA TGT TAA TACAGTTCTT GTACTTCACT      870
Ala Thr Arg Arg Trp Arg His His Lys Cys  *
                    275                 280

GTATGTAAAT ACACAAGGCA CTCTTTTTTA AAAGGACTAT AAATATATAT ATATATATAT      930

ATATATATAT ATAGTAAAAC ATAAAGACTT ATTATAACAG CTGGATTGAG CGCATCCCAT      990

TACCATGCTG AAGAGGAAAT ACTATAAAAT TGCAGCAATT ATATGAACAT TGTATAAACT     1050

GAGCAAATAT TATATGTATA AAGTGAGAAA ATATTAAATA TTTATAACGG AAAAAAAAA      1110

AAAAAAAAAA AAACTCGATC GATGGGATCC                                      1140

(2) INFORMATION FOR SEQ ID NO:4:

(i) SEQUENCE CHARACTERISTICS:
        (A) LENGTH: 280 amino acids
        (B) TYPE: amino acid
        (D) TOPOLOGY: linear (ii) MOLECULE TYPE: protein (xi) SEQUENCE DESCRIPTION: SEQ ID NO:4:

Met Thr Gly Val Phe Leu Leu Leu Cys Ala Ser Met Leu Ala Ala Ala
 1               5                  10                  15

Ala Phe Asp Ile Gly Leu Ser Thr Lys Cys Val Pro Ile Pro Lys Glu
                20                  25                  30

Met Ala Met Cys Asn Asp Val Gly Tyr Ser Glu Met Arg Leu Pro Asn
            35                  40                  45

Leu Leu Gly His Thr Asn Met Ala Glu Val Val Pro Lys Ser Ala Glu
        50                  55                  60

Trp Gln Asn Leu Leu Gln Thr Gly Cys His Pro Tyr Ala Arg Thr Phe
65                  70                  75                  80

Leu Cys Ser Leu Phe Ala Pro Val Cys Leu Asp Thr Phe Ile Gln Pro
                85                  90                  95

Cys Arg Ser Met Cys Val Ala Val Arg Asn Ser Cys Ala Pro Val Leu
                100                 105                 110

Ala Cys His Gly His Ser Trp Pro Glu Ser Leu Asp Cys Asp Arg Phe
            115                 120                 125

Pro Ala Gly Glu Asp Met Cys Leu Asp Thr Leu Ser Lys Glu Tyr Gln
        130                 135                 140

Tyr Ala Tyr Lys Glu Leu Pro Lys Pro Ser Cys Gln Gly Cys Pro Leu
145                 150                 155                 160

Ile Glu Glu Phe Phe Ser His Lys Thr Val Leu Glu Ala Phe Cys Asp
                165                 170                 175

Asn Asn Phe Ala Val Lys Val Lys Leu Ala Lys Lys Thr Thr Ser
                180                 185                 190

Gly Leu His Glu Tyr Glu Thr Glu Gly Pro Val Glu Phe Ile Lys Gln
            195                 200                 205

Gly Leu Leu Leu Pro Tyr Asp Thr Arg Thr Met Ile Glu Gln Trp Leu
        210                 215                 220

Leu Ile Asn Glu Asn Cys Ala Gln Lys Leu Ile Arg Asn Arg Pro Thr
225                 230                 235                 240

Val Tyr Val Ile Ala Gly Asp Ile His His Gly Lys Val Lys Val Asn
                245                 250                 255
```

```
Arg Val Phe His Trp Gln Lys Lys Asp Ser Gln Leu Thr Leu Ala Thr
        260                 265                 270

Arg Arg Trp Arg His His Lys Cys
        275                 280

(2) INFORMATION FOR SEQ ID NO:5:

(i) SEQUENCE CHARACTERISTICS:
        (A) LENGTH: 1146 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 80..967

(xi) SEQUENCE DESCRIPTION: SEQ ID NO:5:

GAATTCCCAT AGCAACAAAC AGTACATCAT TTGGGAAGGA GAAACATTTG TCTTTTGTGC          60

ATCCATAAGG AAAATCCCA ATG GCC CCT CAG CTG TGT CAG AGC CTG GGA AAG         112
                    Met Ala Pro Gln Leu Cys Gln Ser Leu Gly Lys
                      1               5                    10

CCA CTG ATT GTT TTG CTG TGC TTC TTG GCG TGT GGC TCG CAA TCT ATG         160
Pro Leu Ile Val Leu Leu Cys Phe Leu Ala Cys Gly Ser Gln Ser Met
            15                  20                  25

TAT CTG GAC TTC TTT GGC AGC TCC TCA AGA TGC ATG CGA ATC CCA AAG         208
Tyr Leu Asp Phe Phe Gly Ser Ser Ser Arg Cys Met Arg Ile Pro Lys
        30                  35                  40

AGT ATG GCT CTC TGC TAT GAC ATT GGA TAT TCG GAG ATG AGG ATC CCC         256
Ser Met Ala Leu Cys Tyr Asp Ile Gly Tyr Ser Glu Met Arg Ile Pro
    45                  50                  55

AAC TTG CTG GAA CAT GAG ACG ATG GCC GAG GCA ATC CAA CAA TCC TCA         304
Asn Leu Leu Glu His Glu Thr Met Ala Glu Ala Ile Gln Gln Ser Ser
 60                  65                  70                  75

AGC TGG TTA CCT CTT TTG GCA AGA GAG TGC CAT CCT GAT GCA AGA ATA         352
Ser Trp Leu Pro Leu Leu Ala Arg Glu Cys His Pro Asp Ala Arg Ile
            80                  85                  90

TTC CTC TGC TCA CTC TTT GCA CCT ATT TGC TTT GAT CGG TAT ATC TTC         400
Phe Leu Cys Ser Leu Phe Ala Pro Ile Cys Phe Asp Arg Tyr Ile Phe
        95                 100                 105

CCA TGT CGC AGT CTG TGT GAG GCT GTA AGG AGC AGC TGT GCC CCT ATC         448
Pro Cys Arg Ser Leu Cys Glu Ala Val Arg Ser Ser Cys Ala Pro Ile
    110                 115                 120

ATG GCC TGT TAT GGG TAC CCT TGG CCT GAG ATC CTC AAA TGC GAT AAG         496
Met Ala Cys Tyr Gly Tyr Pro Trp Pro Glu Ile Leu Lys Cys Asp Lys
125                 130                 135

TTT CCT GAA GAC CAC GGC ATG TGT ATC TCA ACT ATC ACA AAT GAT ACT         544
Phe Pro Glu Asp His Gly Met Cys Ile Ser Thr Ile Thr Asn Asp Thr
140                 145                 150                 155

GGT TCT ACC CGT AGA ACA GTG CCC CGA GCC AGC TGT AGA GAC TGT GAA         592
Gly Ser Thr Arg Arg Thr Val Pro Arg Ala Ser Cys Arg Asp Cys Glu
                160                 165                 170

CTT GAA GAA GGC AGC ACT TCC AAG GAG ATA CTG GAT ACA TTC TGC CAT         640
Leu Glu Glu Gly Ser Thr Ser Lys Glu Ile Leu Asp Thr Phe Cys His
            175                 180                 185

AAT GAT TTT GTT GCC AAG GTC CGT ATC ACC AAA AAG AAC ATC ACT TCC         688
Asn Asp Phe Val Ala Lys Val Arg Ile Thr Lys Lys Asn Ile Thr Ser
        190                 195                 200

GCT AAC CTT TAC GAC TTT GAT TTG GAT TCC AAA CTT GAG ATC CTG AAA         736
```

```
Ala Asn Leu Tyr Asp Phe Asp Leu Asp Ser Lys Leu Glu Ile Leu Lys
    205                 210                 215

CAC GGC TCG TTA CCC AAA ACA GAC GTC CTT CCT AGG CTT CAG CAG TGG      784
His Gly Ser Leu Pro Lys Thr Asp Val Leu Pro Arg Leu Gln Gln Trp
220                 225                 230                 235

CTG GAT CTG GAT GCT ACC TGT GTG CAG AAT ATC ATG CGT GGG ACC CGC      832
Leu Asp Leu Asp Ala Thr Cys Val Gln Asn Ile Met Arg Gly Thr Arg
                240                 245                 250

ACA GGC GTC TAT GTG ATT TGT GCA GAA GTG CAA GAG GGG AAG GTA GTG      880
Thr Gly Val Tyr Val Ile Cys Ala Glu Val Gln Glu Gly Lys Val Val
            255                 260                 265

GTG AAC AAT GCC TAC GCA TGG CAG AAA AAG AAC AAA AAC CTG CAT TTC      928
Val Asn Asn Ala Tyr Ala Trp Gln Lys Lys Asn Lys Asn Leu His Phe
        270                 275                 280

GCT GTA CGG AAA TGG AAG AAT CAC AAG TGT CGA CCA TAG GAATTCCCAA       977
Ala Val Arg Lys Trp Lys Asn His Lys Cys Arg Pro *
285                 290                 295

TTCGTTGTAC AGAAACCAAA GTCCTGTGTT GTGAAATAGT AGAAGCAGGG GCATTCACGA   1037

GAACTGTATA TAATACTGTA TATATCTATG TTAACTTACT ATAAAACCTT ATTGATAAAA   1097

AAAAAAAAAA AAAAAAAAAA AAAAAAAAAA AAAAAAAAA AACTCGAGC                1146

(2) INFORMATION FOR SEQ ID NO:6:

(i) SEQUENCE CHARACTERISTICS:
        (A) LENGTH: 295 amino acids
        (B) TYPE: amino acid
        (D) TOPOLOGY: linear (ii) MOLECULE TYPE: protein (xi) SEQUENCE DESCRIPTION: SEQ ID NO:6:

Met Ala Pro Gln Leu Cys Gln Ser Leu Gly Lys Pro Leu Ile Val Leu
1               5                   10                  15

Leu Cys Phe Leu Ala Cys Gly Ser Gln Ser Met Tyr Leu Asp Phe Phe
            20                  25                  30

Gly Ser Ser Ser Arg Cys Met Arg Ile Pro Lys Ser Met Ala Leu Cys
        35                  40                  45

Tyr Asp Ile Gly Tyr Ser Glu Met Arg Ile Pro Asn Leu Leu Glu His
    50                  55                  60

Glu Thr Met Ala Glu Ala Ile Gln Gln Ser Ser Ser Trp Leu Pro Leu
65              70                  75                  80

Leu Ala Arg Glu Cys His Pro Asp Ala Arg Ile Phe Leu Cys Ser Leu
            85                  90                  95

Phe Ala Pro Ile Cys Phe Asp Arg Tyr Ile Phe Pro Cys Arg Ser Leu
        100                 105                 110

Cys Glu Ala Val Arg Ser Ser Cys Ala Pro Ile Met Ala Cys Tyr Gly
    115                 120                 125

Tyr Pro Trp Pro Glu Ile Leu Lys Cys Asp Lys Phe Pro Glu Asp His
130                 135                 140

Gly Met Cys Ile Ser Thr Ile Thr Asn Asp Thr Gly Ser Thr Arg Arg
145                 150                 155                 160

Thr Val Pro Arg Ala Ser Cys Arg Asp Cys Glu Leu Glu Glu Gly Ser
            165                 170                 175

Thr Ser Lys Glu Ile Leu Asp Thr Phe Cys His Asn Asp Phe Val Ala
        180                 185                 190

Lys Val Arg Ile Thr Lys Lys Asn Ile Thr Ser Ala Asn Leu Tyr Asp
    195                 200                 205
```

```
Phe Asp Leu Asp Ser Lys Leu Glu Ile Leu Lys His Gly Ser Leu Pro
    210                 215                 220
Lys Thr Asp Val Leu Pro Arg Leu Gln Gln Trp Leu Asp Leu Asp Ala
225                 230                 235                 240
Thr Cys Val Gln Asn Ile Met Arg Gly Thr Arg Thr Gly Val Tyr Val
                245                 250                 255
Ile Cys Ala Glu Val Gln Glu Gly Lys Val Val Asn Asn Ala Tyr
            260                 265                 270
Ala Trp Gln Lys Lys Asn Lys Asn Leu His Phe Ala Val Arg Lys Trp
        275                 280                 285
Lys Asn His Lys Cys Arg Pro
    290                 295
```

(2) INFORMATION FOR SEQ ID NO:7:

(i) SEQUENCE CHARACTERISTICS:
        (A) LENGTH: 502 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
CATGACTGGA GTCTTCCTGC TCCTCTGCGC CTCCATGCTG GCCGCCGCCG CCGCCTTTGA      60
CATTGGATTA TCCACCAAGT GCGTTCCCAT TCCCAAAGAG ATGGCCATGT GCAATGACGT     120
CGGCTACTCG GAGATGCGGT TGCCAAACCT GTTGGGACAC ACTAACATGG CAGAAGTCGT     180
GCCCAAGTCA GCAGAGTGGC AGAACCTCCT ACAGACCGGC TGCCACCCCT ATGCCAGGAC     240
CTTCCTATGC TCCCTATTCG CCCCAGTCTG CCTGGACACG TTCATCCAGC CCTGCCGCAG     300
CATGTGTGTT GCTGTAAGAA ACAGTTGTGC TCCAGTTCTG GCATGTCATG GGCACTCCTG     360
GCCTAAGAGC TTAGACTGTG ACAGGTTCCC AGCTGGGGAA GACATGTGTC TGGACACTCT     420
CAGCAAAGAG TATCAGTATG CCTATAAAGA ACTGCCAAAG CCAAGCTGCC AGGGCTGCCC     480
ACTTATTGAA GAATTCTTTT CA                                              502
```

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

```
CATGGGCAGC TCGAG                                                       15
```

(2) INFORMATION FOR SEQ ID NO:9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
CTGCAGGCGA GCCTGAATTC CTCGAGCCAT CATG                                  34
```

(2) INFORMATION FOR SEQ ID NO:10:

(i) SEQUENCE CHARACTERISTICS:
  (A) LENGTH: 68 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:10:

```
CGAGGTTAAA AAACGTCTAG GCCCCCCGAA CCACGGGAC GTGGTTTTCC TTTGAAAAAC       60

ACGATTGC                                                               68
```

(2) INFORMATION FOR SEQ ID NO:11:

(i) SEQUENCE CHARACTERISTICS:
  (A) LENGTH: 27 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:11:

```
ATACATAGAT TGCGAGCCAC ACGCCAA                                          27
```

(2) INFORMATION FOR SEQ ID NO:12:

(i) SEQUENCE CHARACTERISTICS:
  (A) LENGTH: 27 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:12:

```
ACGCACTTGG TGGATAATCC AATGTCA                                          27
```

(2) INFORMATION FOR SEQ ID NO:13:

(i) SEQUENCE CHARACTERISTICS:
  (A) LENGTH: 10 amino acids
  (B) TYPE: amino acid
  (C) STRANDEDNESS: single
  (D) TOPOLOGY: linear (ii) MOLECULE TYPE: Protein (xi) SEQUENCE DESCRIPTION: SEQ ID NO:13:

```
Phe Leu Cys Xaa Xaa Xaa Ala Pro Xaa Cys
 1               5                  10
```

(2) INFORMATION FOR SEQ ID NO:14:

(i) SEQUENCE CHARACTERISTICS:
  (A) LENGTH: 6 amino acids
  (B) TYPE: amino acid
  (C) STRANDEDNESS: single
  (D) TOPOLOGY: linear (ii) MOLECULE TYPE: Protein (xi) SEQUENCE DESCRIPTION: SEQ ID NO:14:

```
Trp Pro Glu Xaa Leu Xaa
 1               5
```

(2) INFORMATION FOR SEQ ID NO:15:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:15:

Thr Ile Thr Asn Asp Thr
1               5

(2) INFORMATION FOR SEQ ID NO:16:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:16:

Lys Glu Tyr Gln Tyr Ala
1               5

(2) INFORMATION FOR SEQ ID NO:17:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:17:

Lys Glu Tyr Gln Tyr Ala Tyr Lys Glu
1               5

(2) INFORMATION FOR SEQ ID NO:18:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:18:

Trp Xaa Xaa His Lys Cys
1               5